(12) United States Patent
Quinn et al.

(10) Patent No.: US 12,350,476 B2
(45) Date of Patent: Jul. 8, 2025

(54) SYSTEMS, COMPONENTS, AND COMBINATIONS THEREOF FOR PEN-TYPE INJECTION DEVICES

(71) Applicant: Becton, Dickinson and Company, Franklin Lakes, NJ (US)

(72) Inventors: Michael Quinn, Gladstone, NJ (US); Richard Cronenberg, Gladstone, NJ (US); Robert Boyer, Gladstone, NJ (US); Alexander Gorshkov, Gladstone, NJ (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 592 days.

(21) Appl. No.: 17/213,777

(22) Filed: Mar. 26, 2021

(65) Prior Publication Data

US 2021/0299359 A1 Sep. 30, 2021

Related U.S. Application Data

(60) Provisional application No. 63/001,122, filed on Mar. 27, 2020.

(51) Int. Cl.
*A61M 5/315* (2006.01)
*A61M 5/20* (2006.01)

(52) U.S. Cl.
CPC ...... *A61M 5/31551* (2013.01); *A61M 5/2033* (2013.01); *A61M 5/31563* (2013.01)

(58) Field of Classification Search
CPC .......... A61M 5/31551; A61M 5/31563; A61M 5/2033; A61M 5/24; A61M 5/31525; A61M 5/31526; A61M 5/31528; A61M 5/31533; A61M 5/31535; A61M 5/31541; A61M 5/31545; A61M 5/31548; A61M 5/3155; A61M 5/31565; A61M 2005/2403
USPC ........................................................ 604/211
See application file for complete search history.

(56) References Cited

U.S. PATENT DOCUMENTS

| 9,358,344 | B2 | 6/2016 | Pala |
| 9,757,525 | B2 | 9/2017 | Cronenberg et al. |
| 10,357,614 | B2 | 7/2019 | Cronenberg et al. |
| 2012/0283647 | A1 | 11/2012 | Cronenberg et al. |
| 2014/0046268 | A1 | 2/2014 | Quinn et al. |
| 2015/0112274 | A1* | 4/2015 | Quinn ............... A61M 5/31585 604/207 |
| 2016/0235924 | A1 | 8/2016 | Nordisk |
| 2017/0340835 | A1 | 11/2017 | Sanofi |

FOREIGN PATENT DOCUMENTS

| JP | 2017-064536 A | 4/2017 |
| WO | 2019-072826 A1 | 4/2019 |

* cited by examiner

*Primary Examiner* — Lauren P Farrar
(74) *Attorney, Agent, or Firm* — Dickinson Wright PLLC

(57) ABSTRACT

The disclosure provides driver components, systems and drive methods that facilitate improved dose setting, correcting, and/or dispensing in a multiple use pen-type injection device. In particular, various novel braking systems are disclosed that can be implemented within the pen-type injection devices to help achieve the improved dose setting, correcting, and/or dispensing.

6 Claims, 36 Drawing Sheets

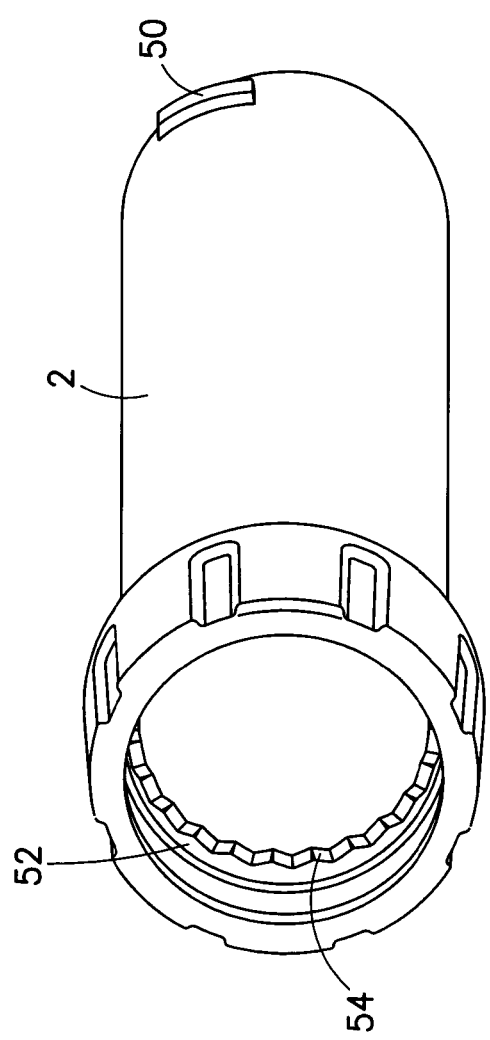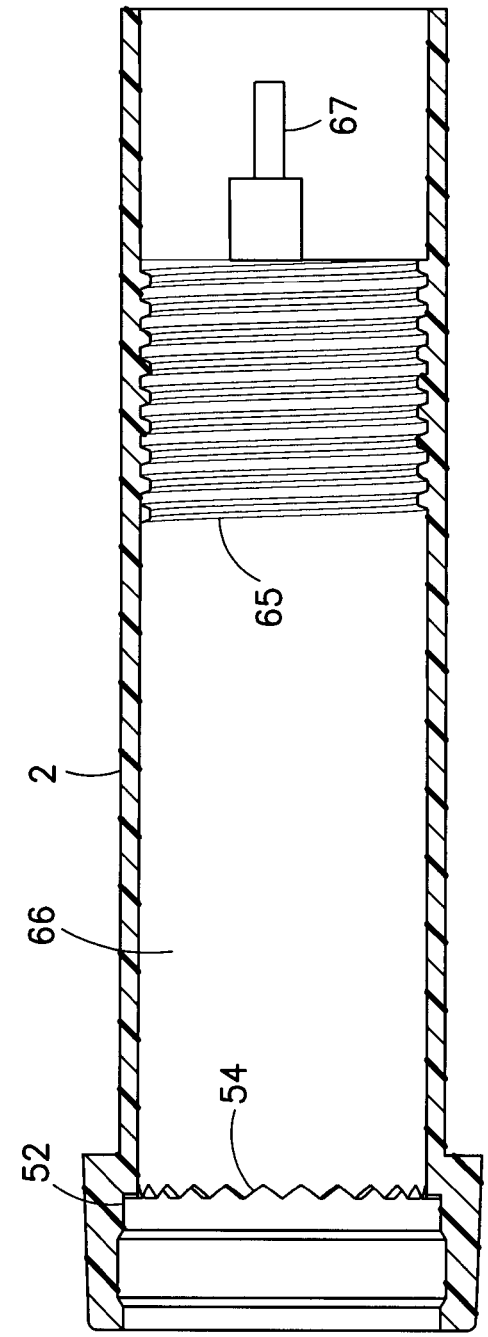

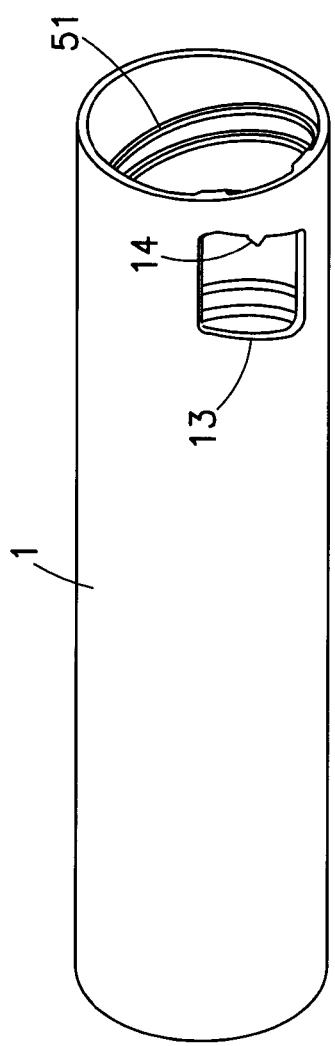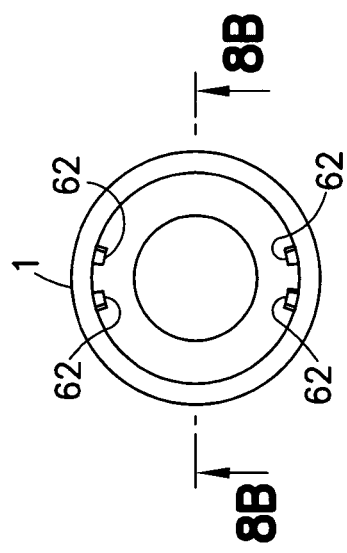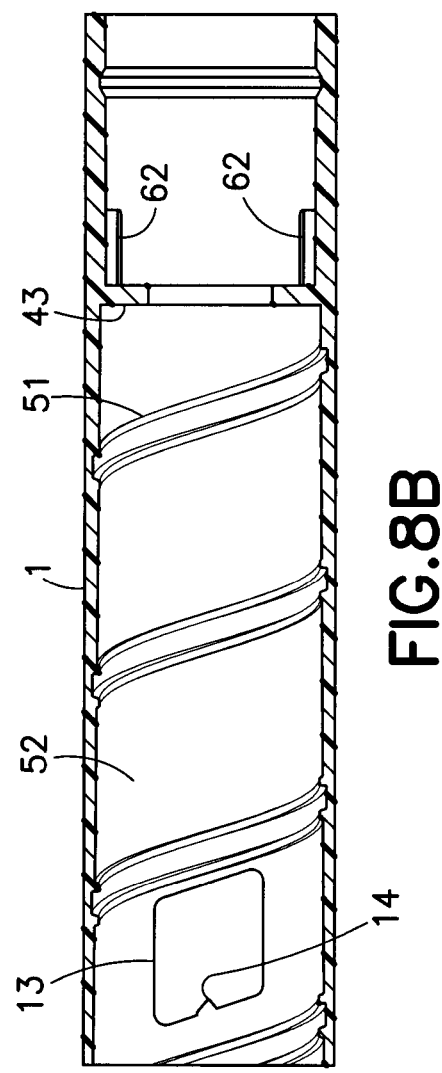

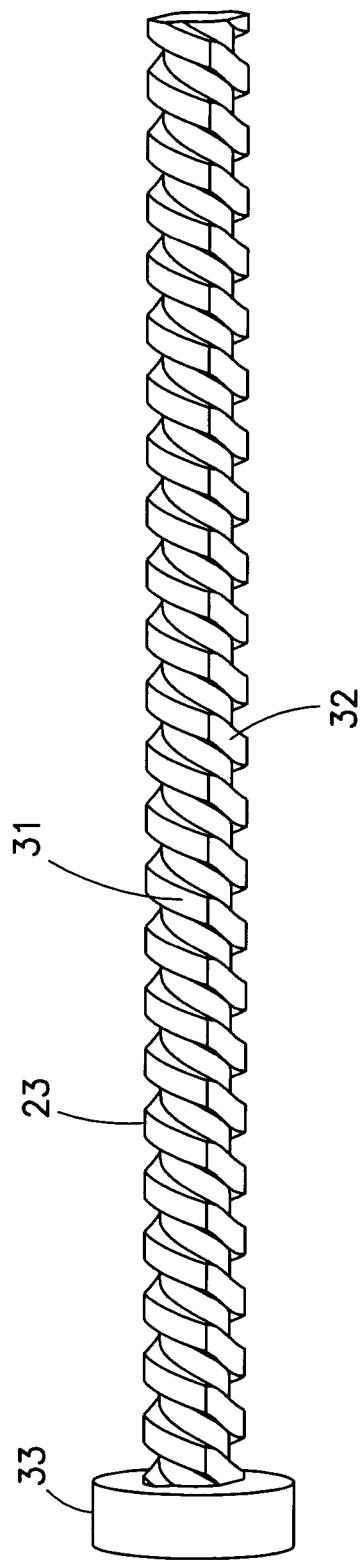
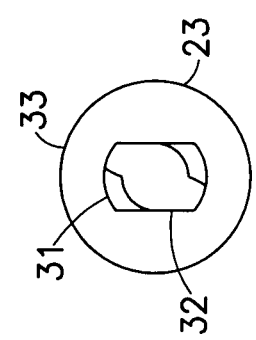
FIG.9A
FIG.9B

SYSTEMS, COMPONENTS, AND COMBINATIONS THEREOF FOR PEN-TYPE INJECTION DEVICES

CROSS-REFERENCE TO RELATED APPLICATIONS

This application claim priority under 35 USC § 119 (e) from U.S. Provisional Patent Applications No. 63/001,122 filed on Mar. 27, 2020, the content of which (including all attachments filed therewith) is hereby incorporated by reference in its entirety.

FIELD OF THE DISCLOSURE

The disclosure relates generally to a multiple use pen-type injection device. More particularly, the present disclosure relates to driver components, systems and drive methods that facilitate improved dose setting, correcting, and/or dispensing in a multiple use pen-type injection device. In this regard, present disclosure is applicable to pen-type injection devices disclosed for example in U.S. Pat. Nos. 9,295,782; 9,757,525; 9,421,334; and 10,357,614, the disclosures of which are incorporated herein by reference in their entirety.

BACKGROUND OF THE DISCLOSURE

Various conventional pen-type injection device are known in the art of medication injection devices. These conventional devices sometimes include features for enabling a user to correct a dose that has been set too large, which may be referred to as "dial back". Another feature that may be provided by some of the conventional devices is the ability to control a last dose of a medication cartridge such that a user cannot set a dose greater than the remaining amount of medication in the cartridge. This feature is sometimes referred to as last dose control or last dose management. Both of these features are desired by users of such pen devices; however, conventional devices may not satisfactorily meet these needs. Many conventional devices may provide one of these features, but not both. Further, many of the conventional devices require additional steps for performing dial back, which are cumbersome and not intuitive to the user.

In addition, conventional pen injection devices commonly include components or mechanism that provide audible and/or tactile signaling and/or feedback during some or all phases of pen operation by the user. Accordingly, many convention injection devices utilize mechanisms, to provide audible and/or tactile feedback during dose setting and/or dose correcting and/or injection.

Thus, there is a need in the art to provide improved functionality of dose setting, dose correcting, dose injecting, last dose control mechanisms, and audible and/or tactile feedback mechanisms, implemented together, individually, or in any combination in a medication injection pen.

SUMMARY OF EMBODIMENTS OF THE DISCLOSURE

Exemplary embodiments of the present disclosure address at least the above problems and/or disadvantages and provide at least the advantages described below.

In accordance with an exemplary embodiment of the present disclosure, a medication injection pen includes a housing and a dose set knob rotatable with respect to the housing. A brake assembly is disposed in the housing has a ratchet member. A driver includes at least one external tooth engaging the ratchet member. The engagement between the ratchet member and the at least one external tooth substantially prevents the driver from rotating with respect to the dose set knob during dose setting and dose correcting. The engagement between the ratchet member and the at least one external tooth allows the driver to rotate with the dose set knob during an injection.

Other exemplary embodiments of the present disclosure, provide various driver systems and mechanisms, each of which can be implemented in medication injection pens as disclosed herein.

Yet other exemplary embodiments of the present disclosure, provide an example of a last dose management system and components, which can be implemented in medication injection pens as disclosed herein including any of the disclosed driver systems and mechanisms.

Yet further exemplary embodiments of the present disclosure, provide an example of an audible and/or tactile feedback mechanisms and components, which can be implemented in medication injection pens as disclosed herein including any of the disclosed driver systems and mechanisms, and/or last dose management system and components.

An exemplary implementation of an embodiments of the present disclosure provides a medication injection pen, comprising: a cartridge housing which houses a medication cartridge; a housing connected to said cartridge housing; a dose set knob rotatable with respect to said housing; a dose stop member to prevent the setting of a dose that is larger than the remaining amount of medication in the cartridge; and a driver, wherein during dose setting and dose correcting, said driver does not rotate with said dose set knob, and said dose stop member rotates relative to said dose set knob, and during an injection, said driver moves into locking engagement with said dose set knob to allow said driver to rotate with said dose set knob, and said dose stop member does not rotate relative to said dose set knob.

An exemplary medication injection pen may further comprise a ratchet disk, said driver rotatably locked to said ratchet disk; and a brake member, wherein said ratchet disc comprises first teeth including first sloped surfaces and first non-sloped surfaces, and said brake member comprises second teeth includes second sloped surfaces and second non-sloped surfaces, during dose setting and dose correcting, said first teeth engage said second teeth to substantially prevent said driver from rotating with said dose set knob, and during an injection, said driver moves into locking engagement with said dose set knob thereby overcoming friction between said first sloped surfaces and said second sloped surfaces to allow said driver to rotate with said dose set knob.

In an exemplary implementation of a medication injection pen, a spring member biases said ratchet member toward said brake member. In another exemplary implementation of a medication injection pen, during said injection, said ratchet disk rotates with said driver and moves against said spring member as said first sloped surfaces ride over said second slope surfaces of said brake member. In yet another exemplary implementation, during said injection, after rotating to a dose increment, said ratchet disk moves into a positions with respect to said brake member where at least one of said first teeth move into a base of next of said second teeth.

In an exemplary embodiment, the medication injection pen can further comprise a brake member; and a ratchet member rotatably locked to said brake member, wherein said ratchet member comprises first teeth including first sloped surfaces and first non-sloped surfaces, and said driver comprises second teeth includes second sloped surfaces and second non-sloped surfaces, during dose setting and dose correcting, said first teeth engage said second teeth to substantially prevent said driver from rotating with said dose set knob, and during an injection, said driver moves into locking engagement with said dose set knob thereby overcoming friction between said first sloped surfaces and said second sloped surfaces to allow said driver to rotate with said dose set knob. In an exemplary implementation, a spring member biases said ratchet member toward said driver. In yet another exemplary implementation, during said injection, said driver rotates forcing said ratchet member to move axially as said first sloped surfaces ride over said second slope surfaces. In still another exemplary implementation, during said injection, after rotating to a dose increment, said ratchet member moves into a positions with respect to said driver where at least one of said first teeth move into a base of next of said second teeth. In still another exemplary implementation, said second teeth are spaced to correspond with the rotation of one dose of medicament. And, in still another exemplary implementation, said ratchet member is a ratchet disc, with an opening configured to receive said driver therethrough.

According to an exemplary embodiment of the disclosure, medication injection pen according can further comprise: a brake member; and a ratchet member comprising ratchet arms, said ratchet member is rotatably locked to said brake member, wherein said driver comprises inward facing ratchet teeth, and said ratchet arms radiate outward toward said inward facing ratchet teeth of said driver, during dose setting and dose correcting, said ratchet arms engage said ratchet teeth to substantially prevent said driver from rotating with said dose set knob, and during an injection, said driver moves into locking engagement with said dose set knob thereby forcing said ratchet arms to flex inward as said ratchet teeth slide past said ratchet arms to allow said driver to rotate with said dose set knob.

In an exemplary implementation, during said injection, after rotating to a dose increment, said ratchet arms move into a base of next of said ratchet teeth. In another exemplary implementation, said ratchet teeth are spaced to correspond with the rotation of one dose of medicament.

According to an exemplary embodiment of the disclosure, medication injection pen according can further comprise: a brake member; and a ratchet member comprising outward facing ratchet teeth, said ratchet member is rotatably locked to said brake member, wherein said driver comprises ratchet arms, and said ratchet arms radiate inward toward said outward facing ratchet teeth, during dose setting and dose correcting, said ratchet arms engage said ratchet teeth to substantially prevent said driver from rotating with said dose set knob, and during an injection, said driver moves into locking engagement with said dose set knob thereby forcing said ratchet arms to flex outward as said ratchet arms slide past said ratchet teeth to allow said driver to rotate with said dose set knob.

In an exemplary implementation, during said injection, after rotating to a dose increment, said ratchet arms move into a base of next of said ratchet teeth. In another exemplary implementation, said ratchet teeth are spaced to correspond with the rotation of one dose of medicament.

According to an exemplary embodiment of the disclosure, medication injection pen according can further comprise: a brake member; and a ratchet member comprising a plate having parabolic waves facing outward toward said brake member, said ratchet member is rotatably locked to said brake member, wherein said driver comprises ratchet teeth including sloped surfaces and non-sloped surfaces, and during an injection, said driver moves into locking engagement with said dose set knob thereby forcing said waves of said ratchet plate to flex to allow said ratchet teeth to rotate past said ratchet plate to allow said driver to rotate with said dose set knob. In an exemplary implementation, during said injection, after rotating to a dose increment, said ratchet teeth move into a wall of next plate cavity. In another exemplary implementation, said ratchet teeth are spaced to correspond with the rotation of one dose of medicament.

According to an exemplary embodiment of the disclosure, medication injection pen according can further comprise: a brake member comprising inward facing ratchet teeth including sloped surfaces and non-sloped surfaces; and wherein said driver comprises flexible ratchet arms that radiate outward toward said inward facing ratchet teeth of said brake member, and during an injection, said driver moves into locking engagement with said dose set knob thereby forcing said flexible ratchet arms to flex inward to slide over said sloped surfaces of said ratchet teeth to allow said driver to rotate with said dose set knob.

In an exemplary implementation, during said injection, after rotating to a dose increment, said ratchet arms move into a base of said ratchet teeth. In another exemplary implementation, said ratchet teeth are spaced to correspond with the rotation of one dose of medicament.

According to an exemplary embodiment of the disclosure, medication injection pen according can further comprise: a brake member rotationally locked to said housing; and a coil spring positioned around said driver, said coil spring is rotationally locked to said brake member and wherein, said coil spring grips said diver prevent preventing said driver from rotating during dose setting by tightening of said coil spring, and during an injection said driver moves into locking engagement with said dose set knob whereby rotation of said driver causes said coil spring to unwind allowing said driver to rotate with said dose set knob.

According to an exemplary embodiment of the disclosure, medication injection pen according can further comprise: a brake member rotationally locked to said housing; and at least one leaf spring rotationally locked to said brake member and positioned radially with respect to said driver, wherein said leaf spring grips said diver prevent preventing said driver from rotating during dose setting by increased tension of said leaf spring, and during an injection said driver moves into locking engagement with said dose set knob whereby rotation of said driver causes said leaf spring to loosen said tension relieving said grip and allowing said driver to rotate with said dose set knob.

According to an exemplary embodiment of the disclosure, medication injection pen according can further comprise: a lead screw including flexible ratchet arms; and a brake member rotationally fixing said lead screw to said housing, wherein said driver comprises inward facing ratchet teeth including sloped surfaces and non-sloped surfaces, said flexible ratchet arms radiate outward toward said inward facing ratchet teeth of said driver, and during an injection, said driver moves into locking engagement with said dose set knob forcing said flexible ratchet arms of said leadscrew to flex inward as they slide over said sloped surfaces of said ratchet teeth to allow said driver to rotate with said dose set knob.

In an exemplary implementation, during said injection, after rotating to a dose increment, said flexible ratchet arms move into a base of said ratchet teeth. In another exemplary implementation, said ratchet teeth are spaced to correspond with the rotation of one dose of medicament.

Additional objects, advantages and salient features of exemplary embodiments of the disclosure, in any combination of features disclosed in exemplary embodiments and implementations described herein, will become apparent to those skilled in the art from the following detailed description, which, taken in conjunction with annexed drawings, discloses exemplary embodiments of the disclosure.

BRIEF DESCRIPTION OF THE DRAWINGS

The above and other exemplary features and advantages of certain exemplary embodiments of the present disclosure will become more apparent from the following description of certain exemplary embodiments thereof when taken in conjunction with the accompanying drawings in which:

FIG. 7A is a perspective view of a dose set knob of FIG. 2;

FIG. 7B is an elevational view in cross-section of the dose set knob of FIG. 7A;

FIG. 8A is a perspective view of a pen upper body of the injection pen of FIG. 2;

FIG. 8B is an elevational view in cross-section of the pen upper body of FIG. 8A;

FIG. 8C is a distal end elevational view of the pen upper body of FIG. 8A;

FIG. 9A is a perspective view of a lead screw of the injection pen of FIG. 2;

FIG. 9B is a distal end elevational view of the lead screw of FIG. 9A;

FIG. 13A;

Throughout the drawings, like reference numerals and like labels will be understood to refer to like elements, features and structures.

DETAILED DESCRIPTION OF EXEMPLARY EMBODIMENTS

The matters exemplified in this description are provided to assist in a comprehensive understanding of exemplary embodiments of the disclosure with reference to the accompanying drawing figures. Accordingly, those of ordinary skill in the art will recognize that various changes and modifications of the exemplary embodiments described herein can be made without departing from the scope and spirit of the claimed disclosure. Also, descriptions of well-known functions and constructions may be omitted for clarity and conciseness.

Figure 1:
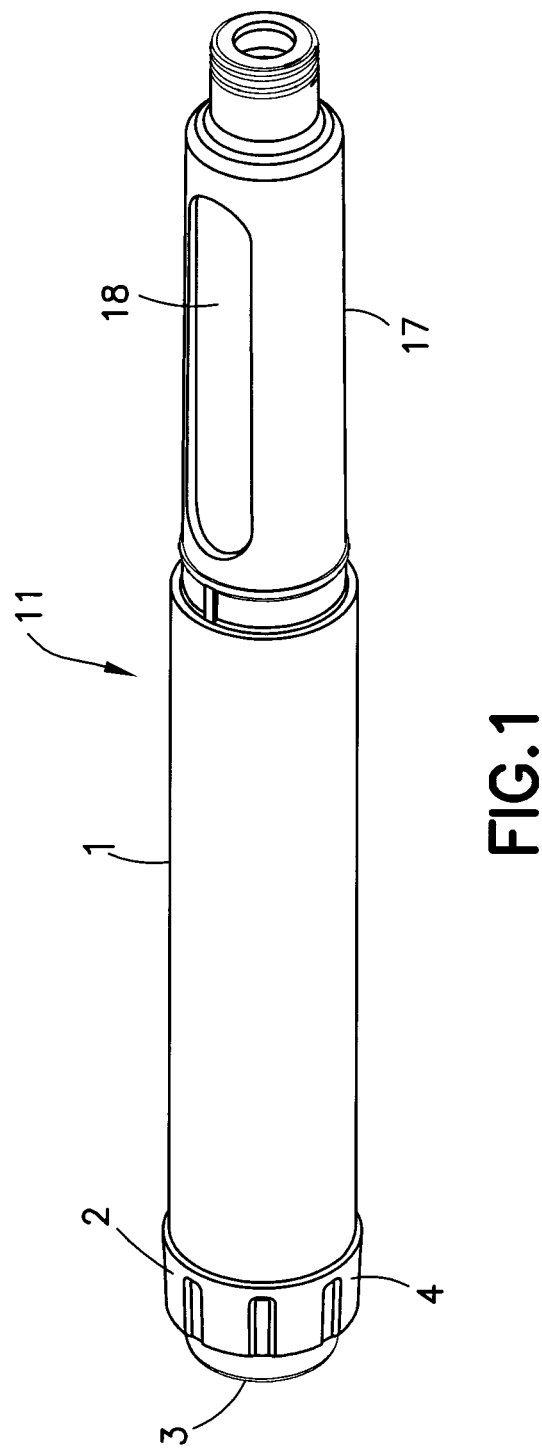
FIG. 1 is a perspective view of an injection pen according to a first exemplary embodiment of the present disclosure.

FIG. 1 is a perspective view of an injection pen 11 according to exemplary embodiments of the present disclosure described in more detail in the context of exemplary implementation shown in FIGS. 1 through 12. Also, an injection pen 11 according to exemplary embodiments of the present disclosure can implement any one of the braking systems which can comprise combinations of various components described in more detail with reference to FIGS. 13A through 22C. Likewise, an injection pen 11 according to exemplary embodiments of the present disclosure can implement audible and/or tactile signaling and/or feedback components/system as disclosed in detail subsequently herein with reference to FIGS. 23-23, for example in combination with any of the disclosed braking systems.

Figure 2:
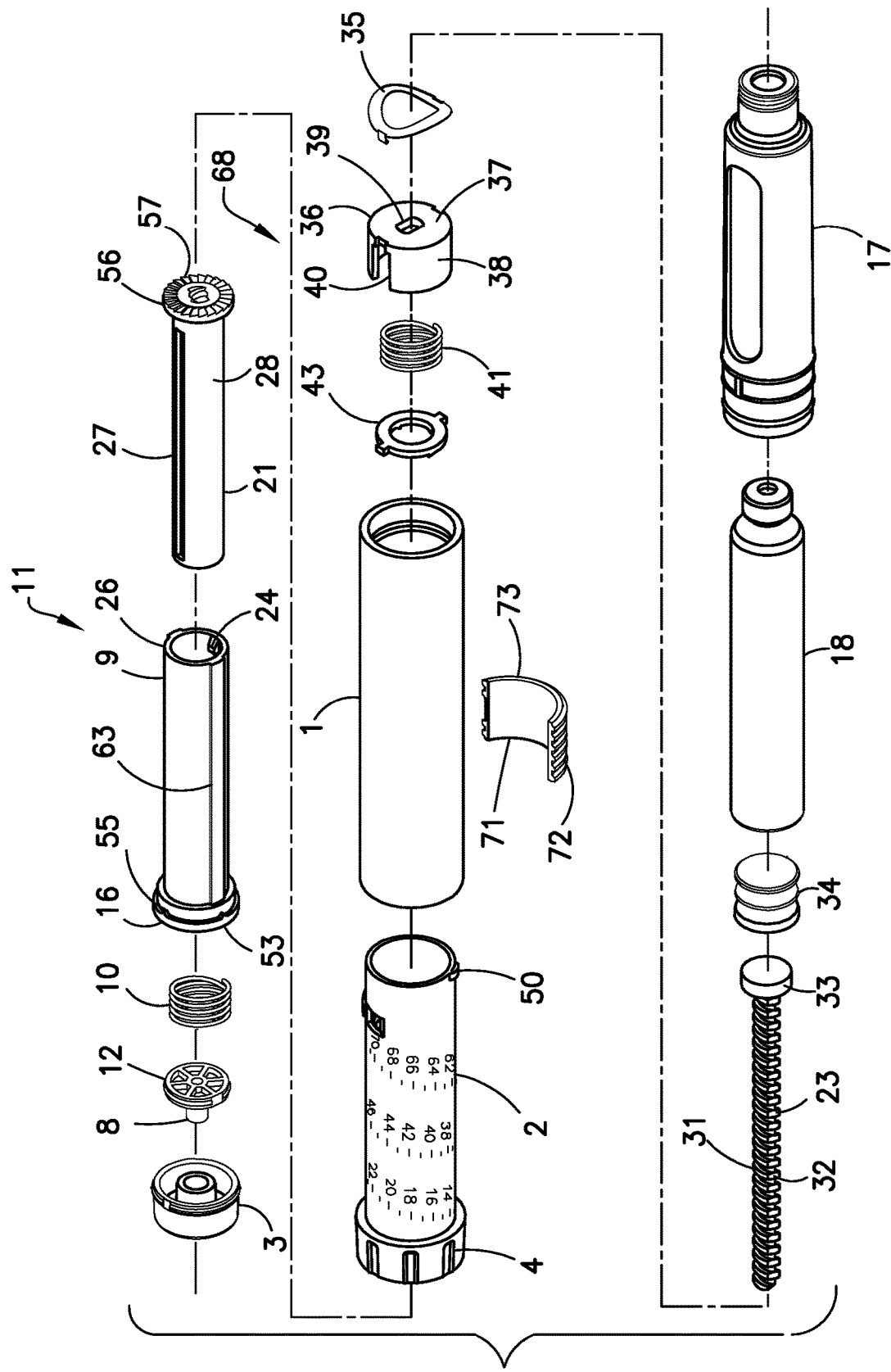
FIG. 2 is an exploded perspective view of the injection pen of FIG. 1.
Figure 3:
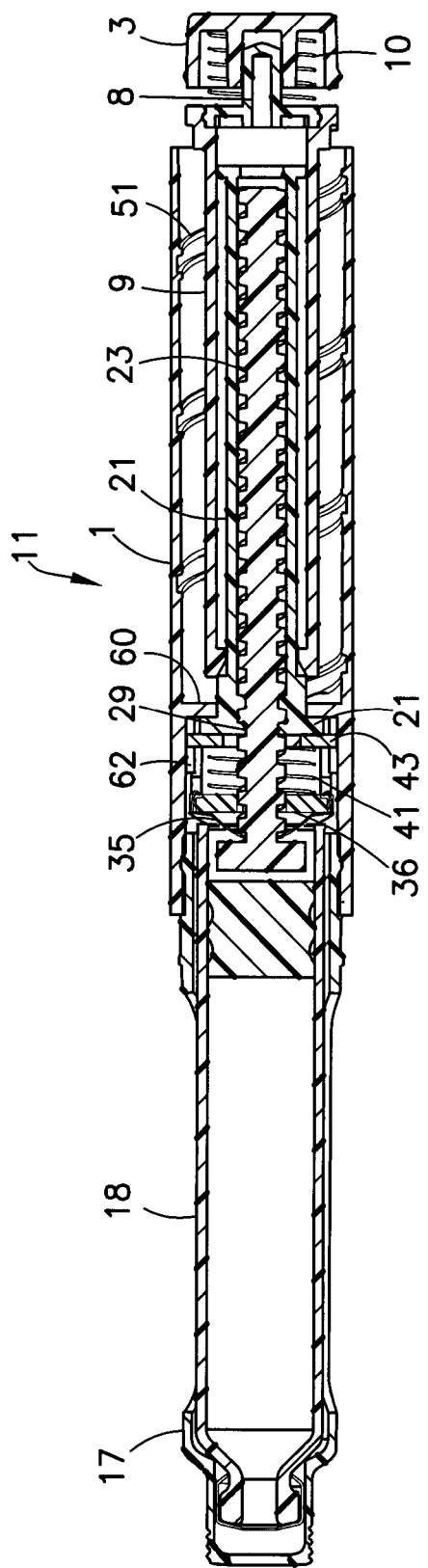
FIG. 3 is an elevational view in cross-section of the injection pen of FIG. 1 without a dose set knob for clarity.

As shown in FIG. 1, the injection pen 11 includes a pen upper body or housing 1, which houses a plurality of dose setting and injection components. The upper body 1 is connected to a cartridge housing 17, which houses a medication cartridge 18, as shown in FIGS. 1 and 3. The injection pen 11 may also include a lower pen cap (not shown) to cover the cartridge 18 and cartridge housing 17 when the injection pen 11 is not in use. As shown, the injection pen 11 includes a dose set knob (DSK) 2 that includes a knob-like portion 4 that is rotated by a user to set a desired dose. The dose set knob 2 also includes a plurality of numerals, as shown in FIG. 2, corresponding to a number of dosage units that is visible through a window 13 provided on the upper body 1, as shown in FIG. 8A. A user rotates the dose set knob 2 until the desired dose is visible in the window 13. The upper pen body 1 may include an arrow or other indicator 14 to precisely indicate the set dose. Once the desired dose is set, a user presses the button 3 until the set dosage amount is completely injected.

Figure 4:
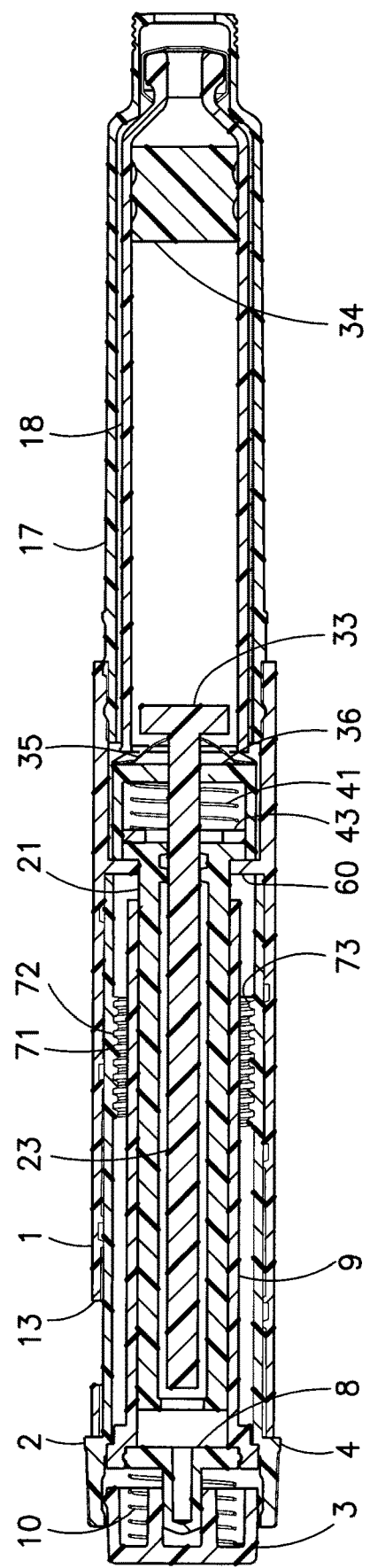
FIG. 4 is an enlarged elevational view in cross-section of the injection pen of FIG. 3 with the dose set knob.

A push button 3 is provided at a proximal end, closest to a user and farthest from a needle (not shown), of the upper pen body 1, as shown in FIG. 4. The push button 3 preferably comprises an annular bead or rim 5 that engages with a corresponding annular groove 6 provided on the internal surface of the knob-like portion 4 of the dose set knob 2. The annular rim/groove connection is preferably a friction fit that maintains the push button 3 in a biased position on the dose set knob 2 under the force of a button spring 10, but allows the push button 3 to be pushed into the dose set knob 2 for injecting a set dose. As shown in FIG. 4, the groove 6 in the knob-like portion 4 of the dose set knob 2 extends axially to allow the push button 3 to be pushed into the dose set knob 2 during an injection. The interior of the button 3 accommodates a setback bearing insert 8 that rests on an internal surface at a proximal end of the setback member 9. As shown in FIG. 4, the bearing insert 8 has an annular rim 12 received by an annular groove 113 (FIG. 5C) adjacent a proximal end 16 of the setback member 9. The push button 3 is designed to rotate freely on the setback bearing insert 8.

Figure 5A:
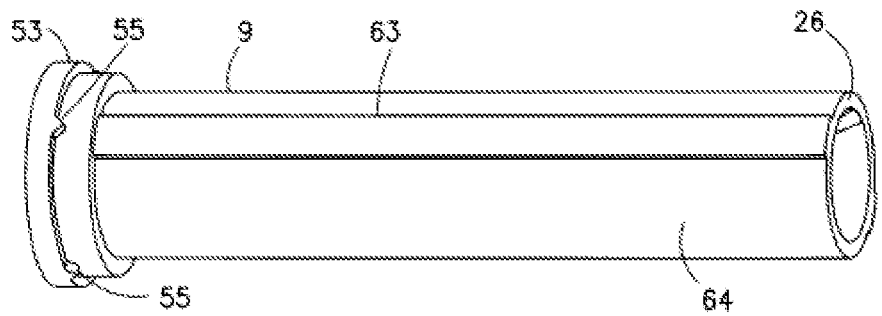
FIG. 5A is a perspective view of a setback member of the injection pen of FIG. 2.
Figure 5B:
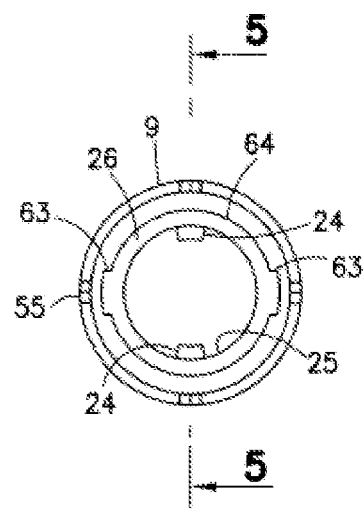
FIG. 5B is a distal end elevational view of the setback member of FIG. 5A.
Figure 5C:
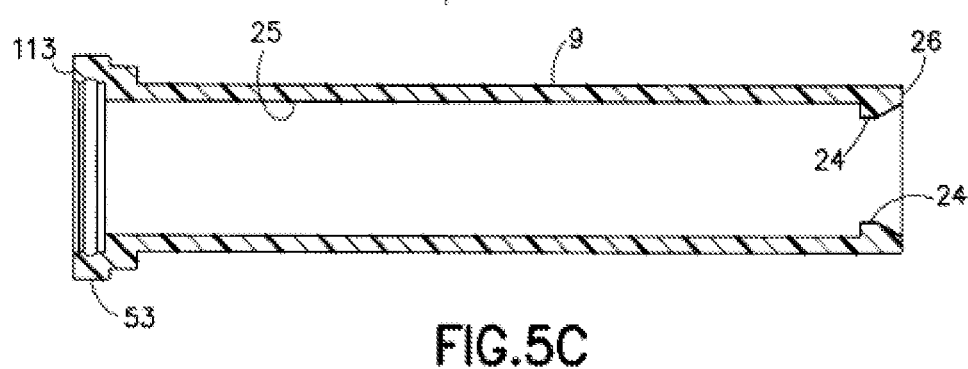
FIG. 5C is an elevational view in cross-section of the setback member of FIG. 5A.
Figure 6A:
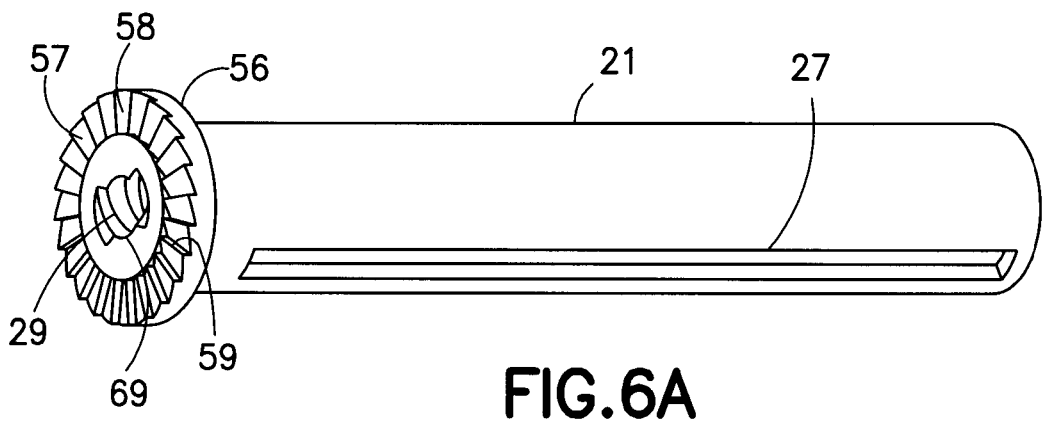
FIG. 6A is a perspective view of a driver of the injection pen of FIG. 2.
Figure 6B:
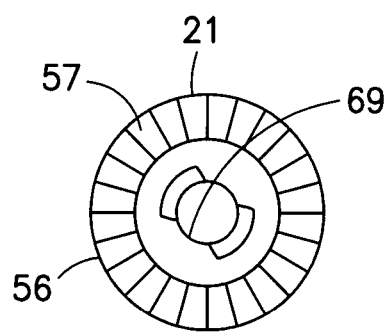
FIG. 6B is a distal end elevational view of the driver of FIG. 6A.
Figure 6C:
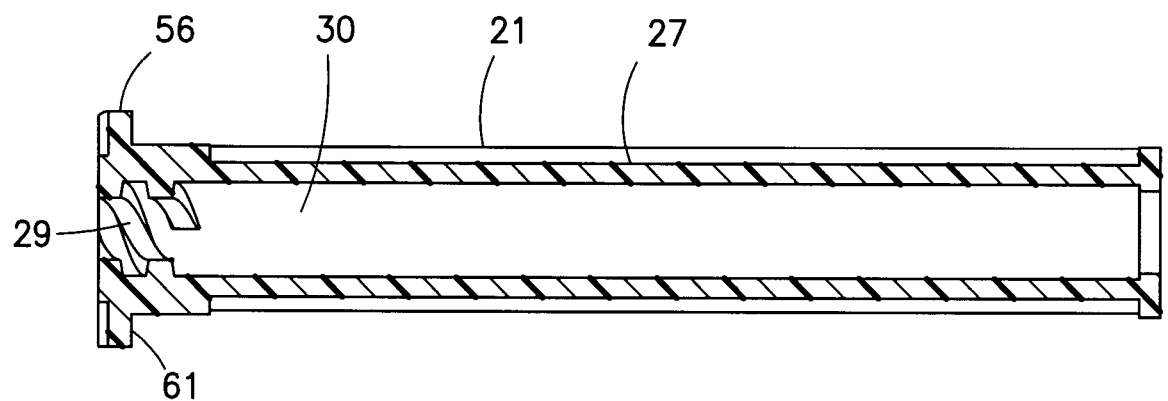
FIG. 6C is an elevational view in cross-section of the driver of FIG. 6A.

The setback member 9 is a cylindrical member, as shown in FIGS. 2 and 5A-5C, coaxial with and surrounded by the dose set knob 2. The setback member 9 is provided co-axially around a driver 21, as shown in FIGS. 3 and 4, that is rotatably fixed to the setback member 9 and axially movable relative to the setback member 9. The driver 21 co-axially surrounds a lead screw 23, as shown in FIGS. 3 and 4. The setback member 9 includes a set of keys 24 extending inwardly from an inner surface 25 at a distal end 26 that engage slots 27 extending axially on an outer surface 28 of the driver 21 to rotatably lock the driver 21 to the setback member 9. The driver 21 has threads 29 on a portion of an inner surface 30 thereof at a distal end of the driver 21, as shown in FIG. 6C. The driver 21 co-axially surrounds a lead screw 23, which includes a plurality of thread segments 31 disposed along substantially an entire axial length of the lead screw 23, as shown in FIGS. 2, 9A and 9B. The plurality of thread segments 31 are oppositely disposed with flattened portions 32 being disposed therebetween. A flange 33 is disposed at a distal end of the lead screw 23 to engage a stopper 34 disposed in the cartridge 18. The driver internal threads 29 are in threaded engagement with the external lead screw threads 31 provided on the lead screw 23. As described further below, due to its threaded engagement with the driver 21, the lead screw 23 is moved into the cartridge 18 during injection to press on a stopper 34 provided inside the cartridge 18 to expel a dose of medication. A flexible spacer, such as for example a wave clip 35 as shown in FIGS. 2 and 3, can be provided between a distal end of a brake member 36 and a proximal end of the cartridge 18 to bias the cartridge 18 in a distal direction to substantially prevent movement of the cartridge 18 during injection, and thus ensure that an accurate dose is injected.

The brake member 36 is disposed in the pen upper body 1, as shown in FIGS. 3 and 4. The brake member 36 is a substantially cylindrical member having a substantially planar base 37 from which a wall 38 extends axially outwardly. An opening 39 in the base 37 receives the lead screw 23. A spring member 41 is disposed on an inner surface 42 of the base of the brake member 36. A ratchet disk 43 is disposed on the spring member 41. The ratchet disk 43 is preferably circular with an opening 44 therein to receive the lead screw 23. A pair of keys 45 extend outwardly from the ratchet disk 43 to engage the slots 40 in the brake member 36. The slots 40 substantially prevent rotational movement of the ratchet disk 43, while allowing axial movement of the ratchet disk 43. A plurality of teeth 46 extend upwardly from an upper surface 47 of the ratchet disk 43. Each tooth 46 has a sloped surface 48 forming an obtuse angle with the upper surface 47 and a stopping surface 49 disposed substantially perpendicularly to the upper surface 47.

To set a dose using the injection pen device of the first exemplary embodiment, a user rotates the knob-like portion 4 of the dose set knob 2 relative to the pen upper body 1. The outer surface of the dose set knob 2 includes a thread 50, as best shown in FIGS. 2 and 7A, that is in threaded engagement with a plurality of threads 51 provided on an internal surface 52 of the upper pen body 1, as shown in FIGS. 2 and 8C. Accordingly, as the dose set knob 2 is rotated relative to the upper pen body 1, the dose set knob 2 screws or advances a distance out of the upper pen body 1. The dose set knob 2 includes an annular shoulder or rim 52 on the interior surface thereof near the proximal end, as shown in FIGS. 7A and 7B. The annular shoulder 52 engages with an enlarged portion or head 53 of the setback member 9, as shown in FIGS. 2, 5A and 5C. The annular shoulder 52 of the dose set knob 2 preferably comprises a series of teeth or ridges 54 that engage with a plurality of similarly shaped teeth or ridges 55 provided on the enlarged head 53 of the setback member 9. During dose setting, the dose set knob 2 is free to rotate with respect to the setback member 9 in both a clockwise and counter-clockwise direction. As this occurs, the plurality of teeth or ridges 54 of the dose set knob 2 slip past the teeth 55 provided on the enlarged head portion 53 of the setback member 9, thus providing a tactile signal or clicking noise indicating the setting of a dose unit. As further described below, the dose set knob 2 is enabled to rotate relative to the setback member 9 during setting due to a one-way ratchet that prevents the setback member 9 from rotating together with the dose set knob 2 in the setting direction.

Rotation of the dose set knob 2 in the dose setting direction is not transferred to the setback member 9 due to the one-way ratchet between the driver 21 and the ratchet disk 43, as shown in FIG. 3. The setback member 9 near its distal end includes a pair of keys 24, as shown in FIGS. 2 and 5C. The pair of keys 24 engages respective slots 27 in the driver 21, as shown in FIGS. 2 and 6A. The keys 24 and slots 27 rotationally lock the setback member 9 and the driver 21 together while allowing for axial movement of the setback member 9. A flange 56 disposed at a distal end of the driver 21 has a plurality of teeth 57 disposed on a lower surface thereof. The driver teeth 57 have sloped surfaces 58 and stopping surfaces 59, as shown in FIG. 6A. The stopping surfaces 59 of the driver teeth 57 engage the stopping surfaces 49 of the ratchet disk teeth 46, thereby preventing rotation of the driver 21. The spring member 41 biases the ratchet disk 43 into engagement with the driver flange to facilitate preventing rotation of the driver 21. Accordingly, preventing the driver 21 from rotating also prevents the setback member 9 from rotating. As the dose set knob 2 is rotated out of the pen upper body 1 during dose setting, the engagement between the enlarged head portion 53 of the setback member 9 and the shoulder 52 of the dose set knob 2 causes the setback member 9 to move axially as the keys 24 slide within the driver-slots 27. As noted above, the dose set knob teeth 54 slip past the setback member teeth 55 during dose setting to provide a clicking noise to indicate to the user that a dose is being set.

To correct a set dose that may have been set too high, the user rotates back the dose set knob 2 in the opposite direction. Rotation of the dose set knob 2 in this direction is not transferred to the setback member 9 due to the one-way ratchet between the driver 21 (to which the setback member 9 is rotationally fixed) and the ratchet disk 43, as shown in FIG. 3. The friction between the teeth 54 and 55 of the dose set knob 2 and the setback member 9 is not large enough to overcome the friction between the driver flange 56 and the spring-biased ratchet disk 43. Thus, the dose set knob 2 can be rotated back to correct a set dose without causing rotation of the setback member 9 in this direction, although the setback member 9 will move axially due to the engagement of the setback member keys 24 in the slots 27. Accordingly, the dose set knob teeth 54 slip past the setback member teeth 55, which is prevented from rotating, to provide a clicking noise during dialing back of the dose, just as during normal dose setting.

As the dose set knob 2 screws or advances axially out of the upper body 1 during the setting of a dose, the setback member 9 is also caused to move axially out of the body a corresponding distance. This axial movement is caused by the engagement between the annular shoulder 52 on the dose set knob 2 pushing against the enlarged head portion 53 of the setback member 9 during its movement out of the pen upper body 1. Once a desired dose is set, the user pushes the push button 3 that is coupled to the setback bearing insert 8 that is axially connected to the setback member 9. Under the force applied by the user pressing the push button 3, the setback member 9 is moved into a locking or meshing engagement with the dose set knob 2 via a meshing of the respective teeth or ridges 55 and 54 provided on the setback member 9 and the dose set knob 2, respectively. As the user continues to press the push button 3, the dose set knob 2 is caused to rotate and screw back down into the pen upper body 1 via the thread engagement between the thread 50 on the dose set knob 2 and the thread 51 in the pen upper body 1. Rotation of the dose set knob 2 is then transferred to the setback member 9 due to their locking or meshed engagement. The force of the user pressing the button 3 is enough to overcome the friction between the disk ratchet 43 and the driver flange 56, and as a result, the setback member 9 is enabled to rotate in this direction.

Rotation of the setback member 9, as allowed during injection, is then transferred to the driver 21, which is rotatably fixed to the setback member 9 via a key groove connection provided between the driver 21 and the setback member 9. As shown in FIGS. 5B and 5C, the internal surface 25 of the setback member 9 has inwardly extending keys 24 that engage axially extending slots 27 in the driver 21, as shown in shown in FIG. 3. The setback member 9 preferably includes two oppositely disposed keys 24 for engaging two oppositely disposed slots 27 in the driver 21. The setback member 9 moves axially relative to the driver 21 during dose setting and dose correcting, via the key 24 and slot 27 interconnection as shown in FIG. 3. The length of the slot 27 in the driver 21 can be configured to correspond to a maximum allowed dose to be injected in a single injection. The driver 21 is axially fixed with respect to the pen upper body 1 by a transverse wall 60. An upper surface 61 of the flange 56 abuts the transverse wall 60 of the pen upper body 1. The spring member 41 biases the driver flange 56 into contact with the transverse wall 60 through the ratchet disk 43.

As the setback member 9 rotates with the dose set knob 2 during injection, the driver 21 is rotated with the setback member 9. The sloped surfaces 58 and 46 of the driver teeth 57 and the ratchet disk teeth 46 engage such that the driver 21 rotates relative to the ratchet disk 43. The spring member 41 biases the ratchet disk 43 into contact with the driver flange 56, thereby generating a tactile signal and/or clicking noise as the driver teeth 57 slip over the ratchet disk teeth 46. The outwardly extending keys 45 of the ratchet disk 43 are received in the brake member slots 40, thereby preventing rotation of the ratchet disk 43.

As described above, the lead screw 23 includes a plurality of thread segments 31 that are in threaded engagement with threads 29 of the partially threaded driver 21, as shown in FIG. 3. Preferably, only a few thread segments are provided at a distal end of the driver 21 as shown in FIG. 6C. The lead screw 4 is held non-rotatable with respect to the upper pen body 1 by the opening 39 in the brake member 36. The opening 39 has a shape corresponding to the shape of the lead screw 4, which is flattened sides, such that the lead screw 4 is prevented from rotating relative to the brake member 36. The brake member 36 is prevented from rotating relative to the pen upper body 1 due to the engagement between the slots 40 in the brake member 36 and axially extending ribs 62 extending distally from the transverse wall 43, as shown in FIGS. 3, 8B and 8C. The rotation of the axially fixed driver 21 rotates the lead screw 23 through the threaded engagement therebetween, thereby driving the lead screw 23 distally into the cartridge 18. The axial movement of the lead screw 23 pushes the stopper 34 distally into the cartridge 18 to expel medicament stored therein.

Figure 10:
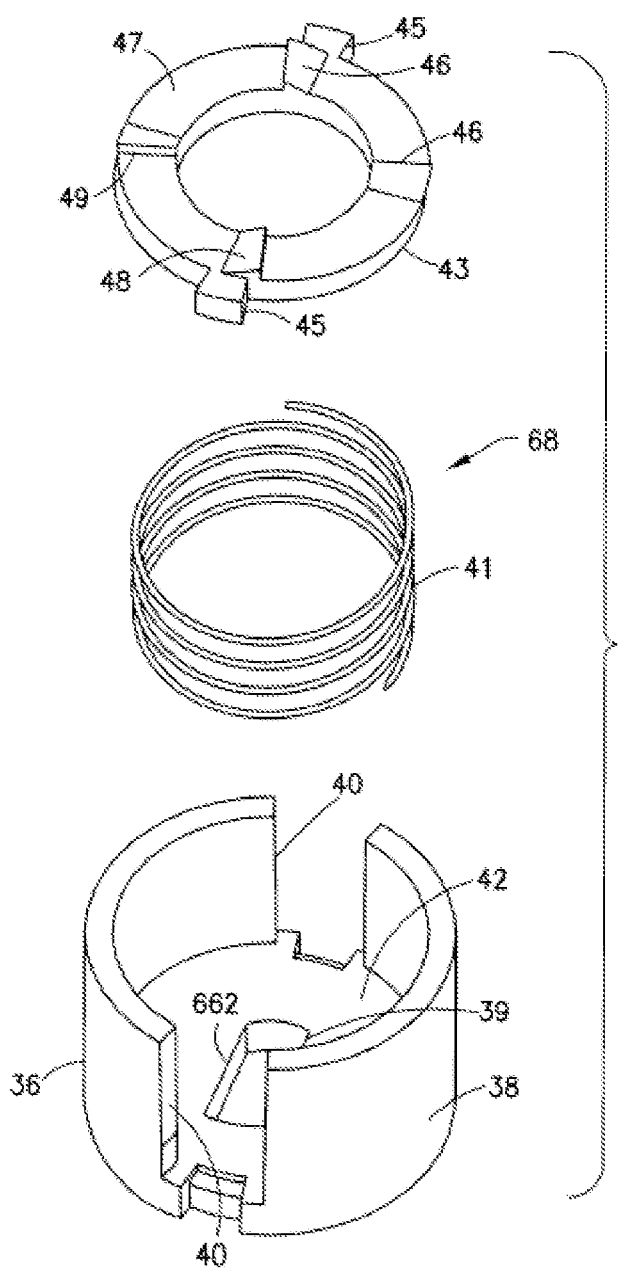
FIG. 10 is an exploded assembly view of a brake assembly of the injection pen of FIG. 2.
Figure 11A:
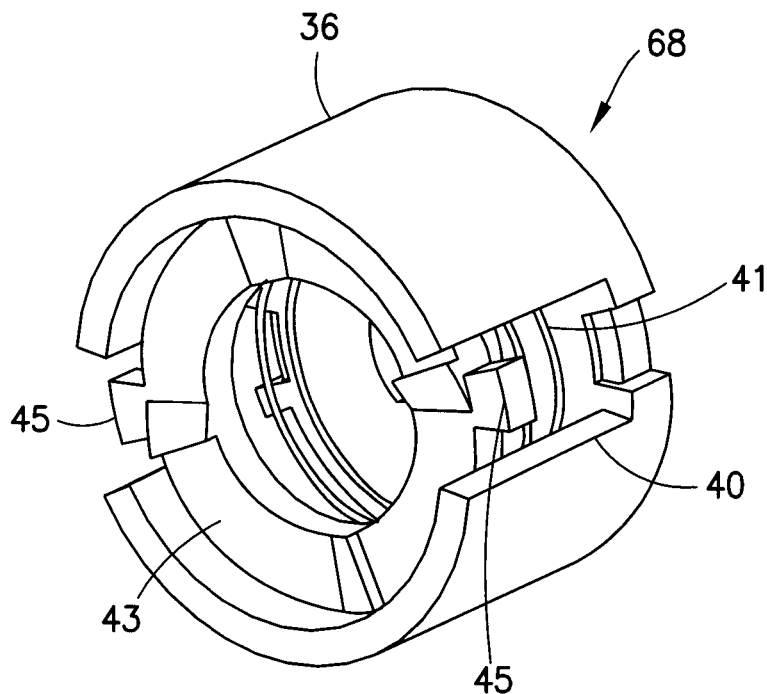
FIG. 11A is a perspective view of the brake assembly of FIG. 10.
Figure 11B:
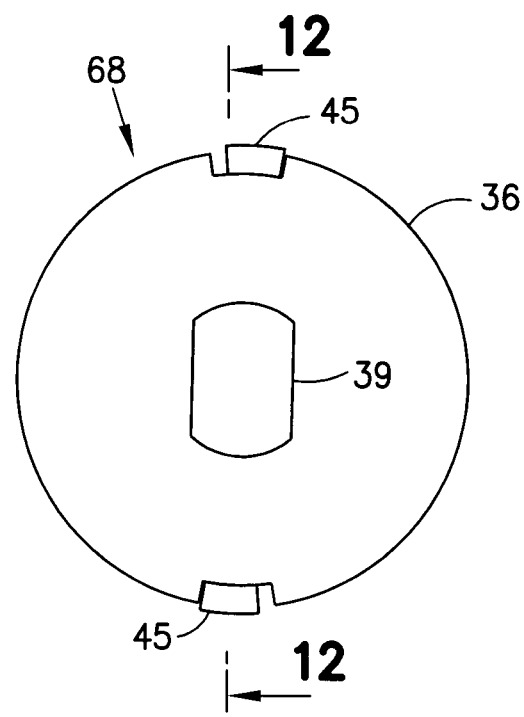
FIG. 11B is a distal end elevational view of the brake assembly of FIG. 11A.
Figure 11C:
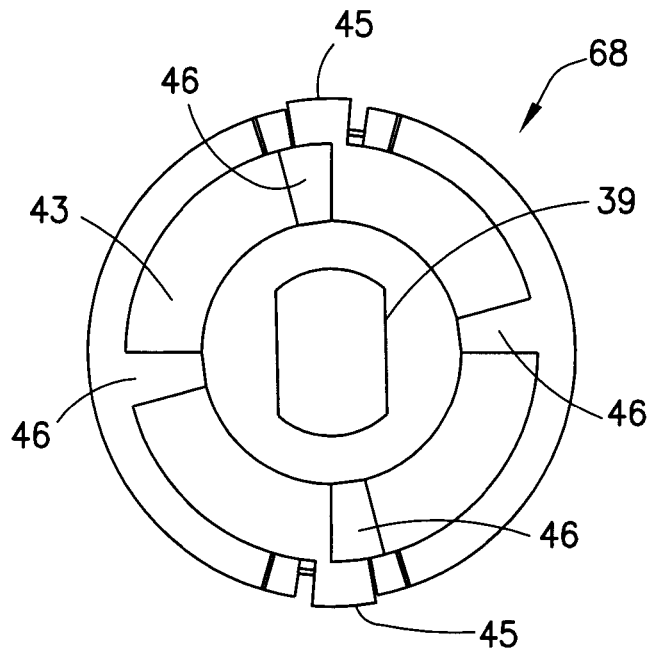
FIG. 11C is a proximal end elevational view of the brake assembly of FIG. 11A.
Figure 12:
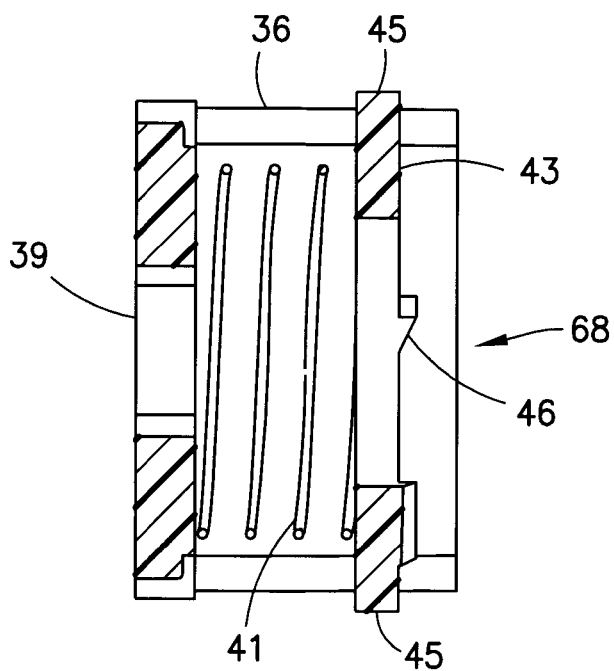
FIG. 12 is an elevational view in cross section of the brake assembly of FIG. 10.

According to an exemplary implementation, during assembly, the driver 21 is inserted in the pen upper body 1 from the distal end. The brake assembly 68 includes the brake member 36, the spring member 41 and the ratchet disk 43, as shown in FIGS. 10-12. The brake assembly 68 is inserted in the pen upper body 1 from the distal end. The lead screw 23 is inserted through the opening 39 in the brake member 36 and through an opening 69 in the driver 21. The driver 21 is then rotated to draw the lead screw 23 proximally. The slots 40 in the brake member 36 rotationally fix the brake member 36 to the pen upper body 1. The flattened sides 662 of the brake member opening 39 receive the flattened portions 32 of the lead screw threads 31 to prevent rotation of the lead screw 23 and limit the lead screw to axial movement.

Exemplary embodiments of braking systems that can be implemented within pen-type injection devices such as those, but without limitation, described above, will now be described with reference to FIGS. 13A through 22C, where analogous components are referenced by similar, non-limiting descriptive, terms.

Figure 13A:
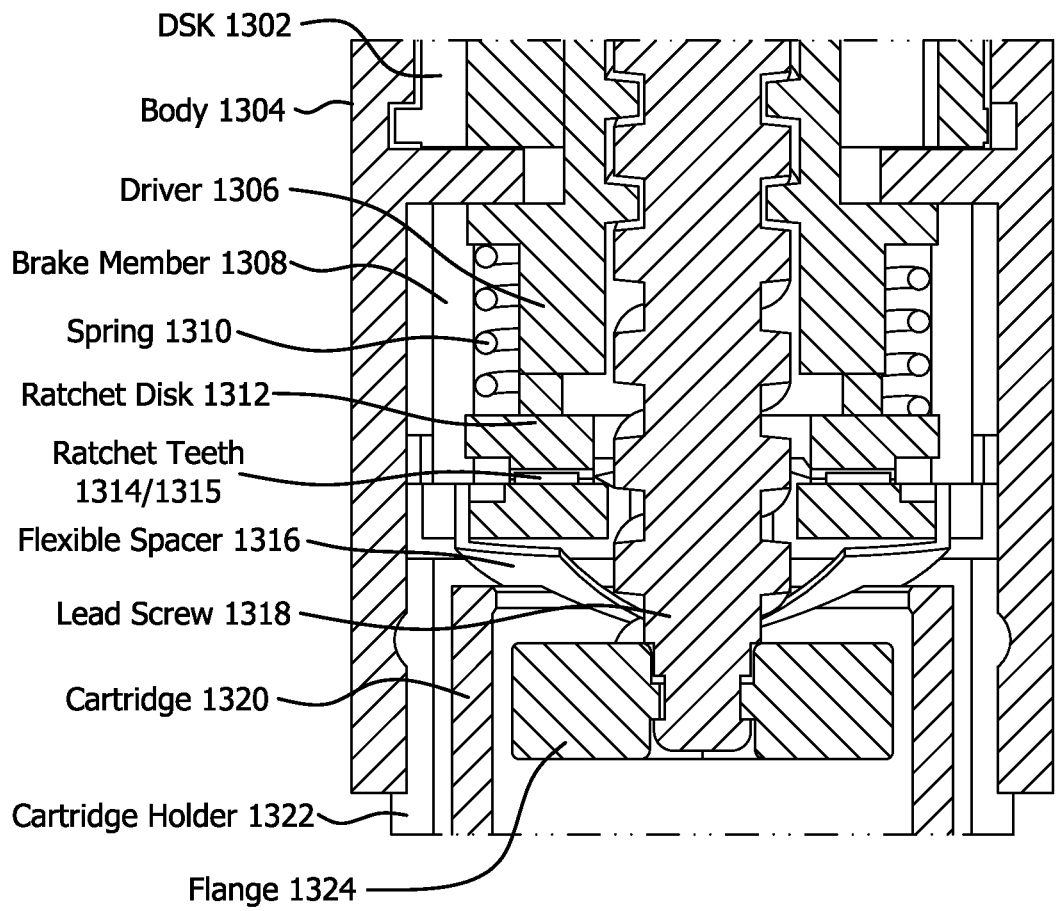
FIG. 13A is a partial cross-section view of a drive system for an injection pen according to an embodiment of the present disclosure.
Figure 13B:
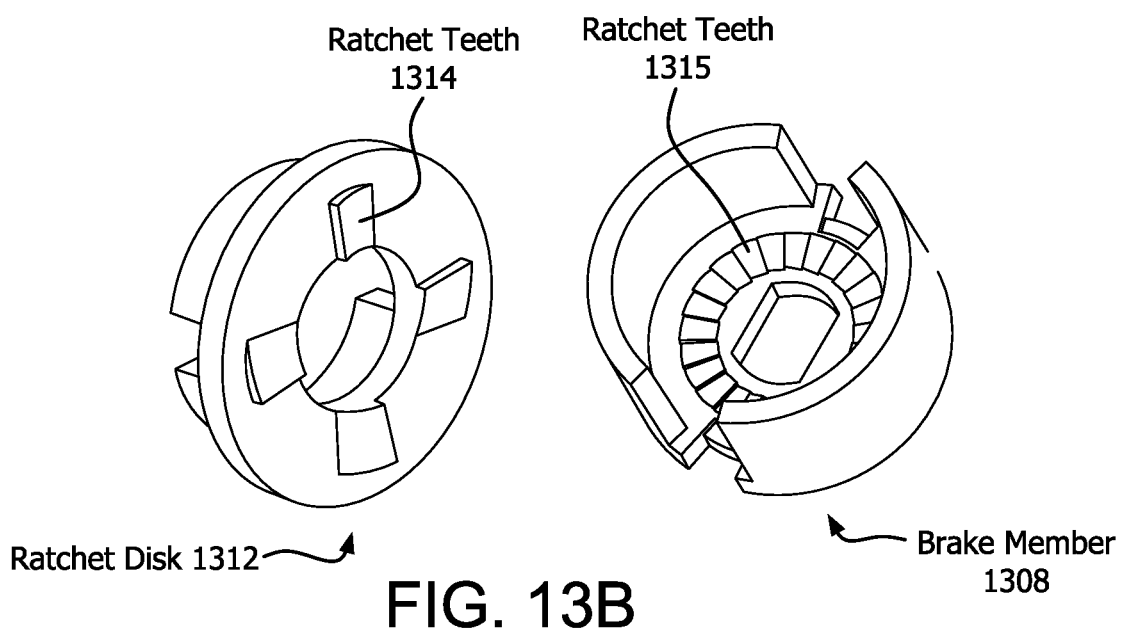
FIG. 13B is an perspective view of certain components of the drive system of FIG. 13A.
Figure 13C:
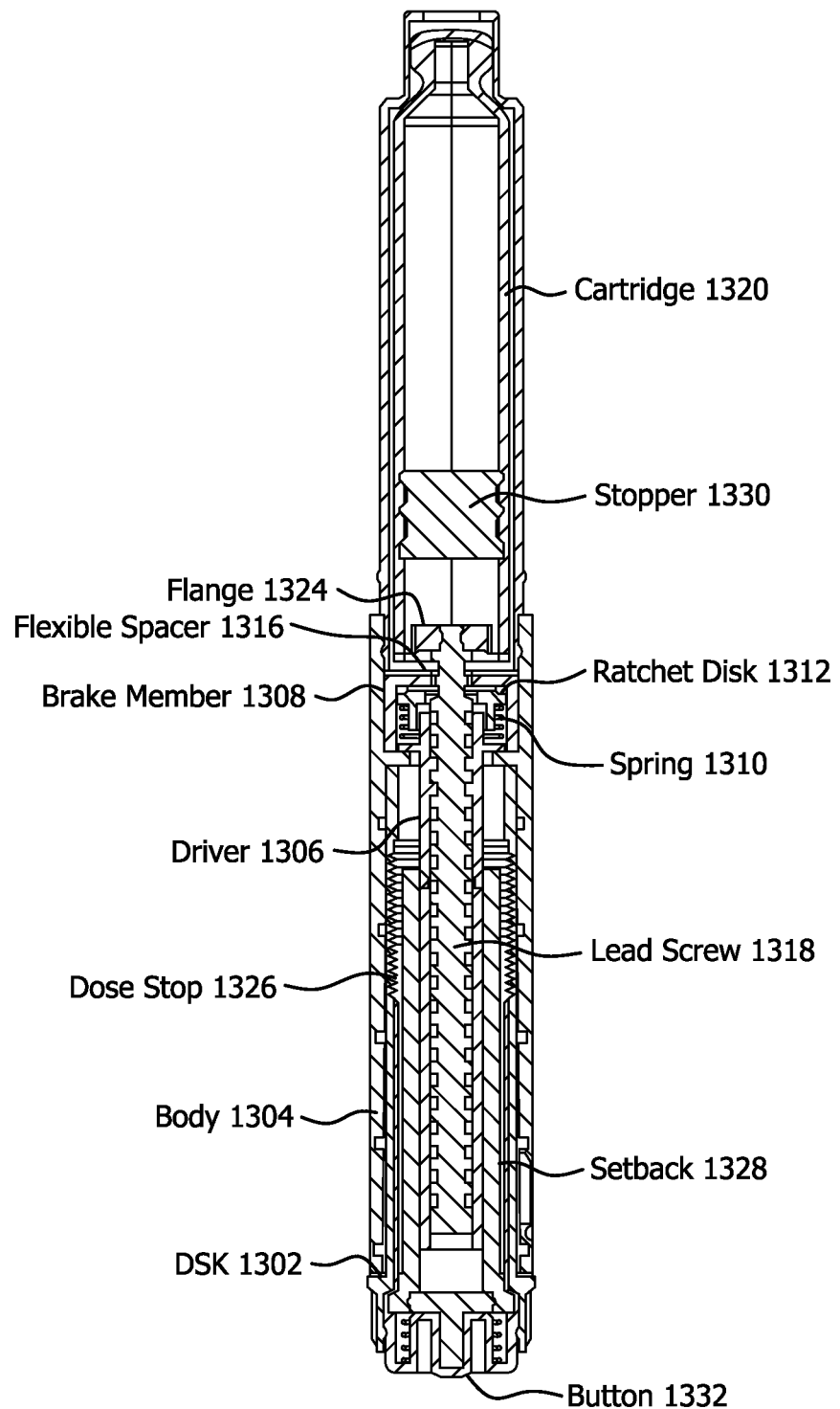
FIG. 13C is a cross-section view of a diagrammatical representation of an injection pen implementing the drive system of FIG. 13A.

Referring to FIGS. 13A, 13B, and 13C, an exemplary embodiment of a braking system includes a Driver 1306 rotatably locked to a Ratchet Disk 1312. An example of a pen-type injection device implementing such a braking system includes, for example as described above but without limitation and in any combination, other components such as: a button 1332, DSK 1302, setback 1328, and dose stop 1326 disposed in body 1304; flexible spacer 1316, lead screw 1318, cartridge 1320 containing medicament, cartridge holder 1322 (which contains cartridge 1320 and, for example can be removably attached to the body 1304 interacting with spacer 1316); and flange 1324 disposed at a distal end of the lead screw 1318 to engage a stopper 1330 disposed in the cartridge 1320. The Spring 1310 biases the Ratchet Disk 1312 toward the distal end of the pen. The Ratchet Disk 1312 has sloped surfaces facing the driven direction, and non-sloped surfaces facing the "dial" direction and constitute ratchet teeth 1314. These teeth 1314 interact with opposing teeth 1315 in the Brake Member 1308, which are spaced to correspond with the rotation of one dose of medicament. During dose injection the Ratchet Disk 1312 rotates with the Driver 1306 and also moves rearward against the Spring 1310 as sloped teeth surfaces of teeth 1314 ride over the teeth 1315 of the Brake Member 1308. After rotating to one dose increment the Ratchet Disk 1312 "clicks" into the base of the next sloped tooth 1315.

Figure 14A:
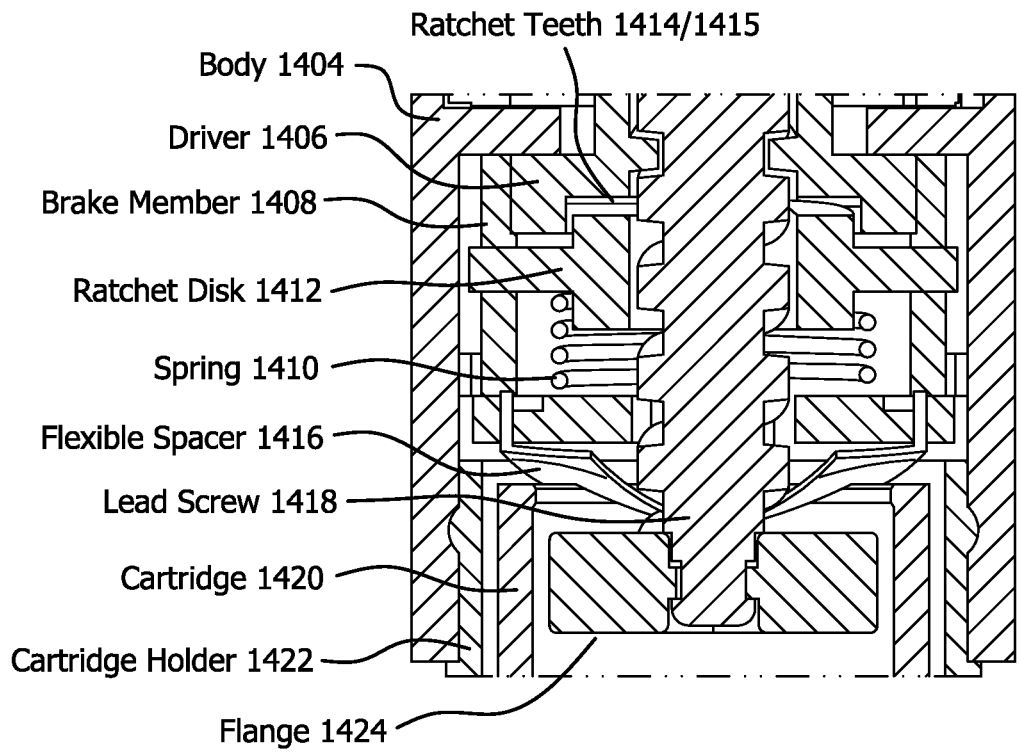
FIG. 14A is a partial cross-section view of a drive system for an injection pen according to an embodiment of the present disclosure.
Figure 14B:
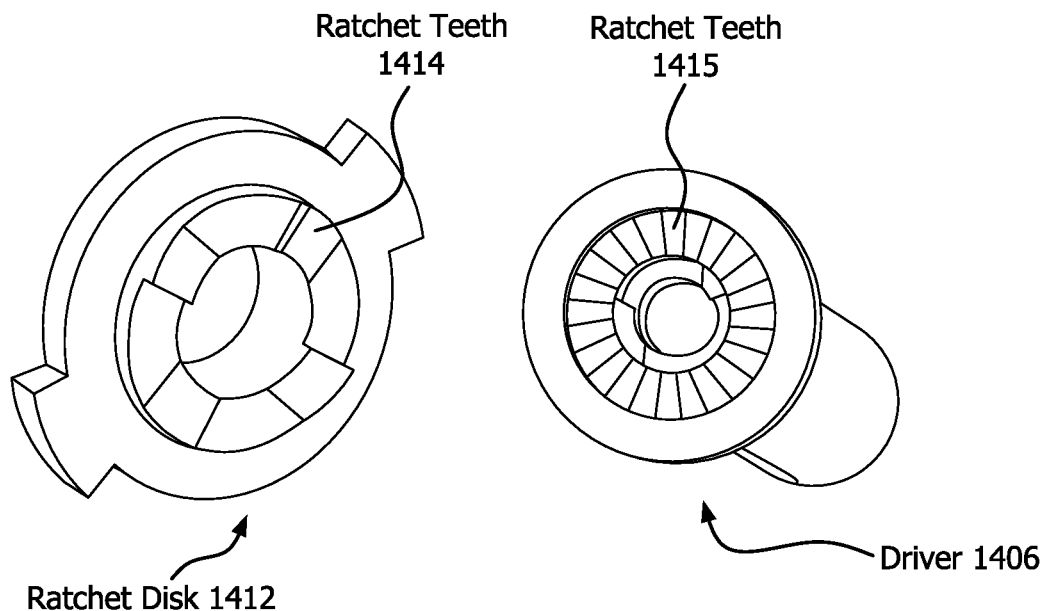
FIG. 14B is an perspective view of certain components of the drive system of FIG. 13A.
Figure 14C:
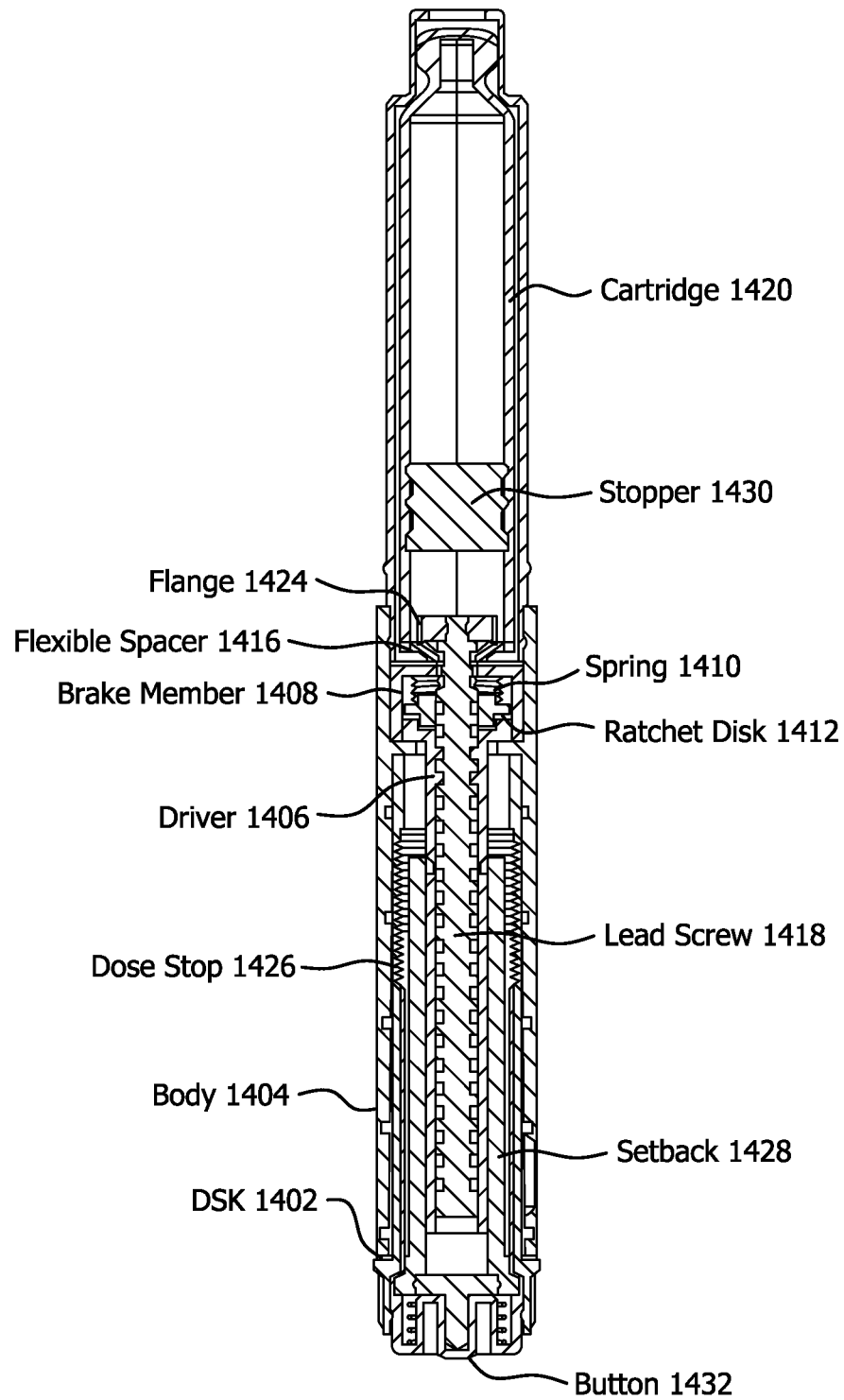
FIG. 14C is a cross-section view of a diagrammatical representation of an injection pen implementing the drive system of FIG. 13A.

Referring to FIGS. 14A, 14B, and 14C, an exemplary embodiment of a braking system includes a Ratchet Disk 1412 rotatably locked to a Brake Member 1408. An example of a pen-type injection device implementing such a braking system includes, for example as described above but without limitation and in any combination, other components such as: a button 1432, DSK 1402, setback 1428, and dose stop 1426 disposed in body 1404; flexible spacer 1416, lead screw 1418, cartridge 1420 containing medicament, cartridge holder 1422 (which contains cartridge 1420 and, for example can be removably attached to the body 1404 interacting with spacer 1416); and flange 1424 disposed at a distal end of the lead screw 1418 to engage a stopper 1430 disposed in the cartridge 1420. The Spring 1410 biases the Ratchet Disk 1412 toward the proximal end of the Driver 1406. The Ratchet Disk 1412 has sloped surfaces facing the driven direction, and non-sloped surfaces facing the "dial" direction and constitute ratchet teeth 1414. The teeth 1414 interact with opposing teeth 1415 on the Driver 1406, which are spaced to correspond with the rotation of one dose of medicament. During dose injection the Driver 1406 rotates, forcing the Ratchet Disk 1412 to move axially as the ratchet teeth 1414/1415 slide past each other. After rotating to one dose increment the Ratchet Disk 1412 "clicks" into the base of the next sloped tooth 1415.

Figure 15A:
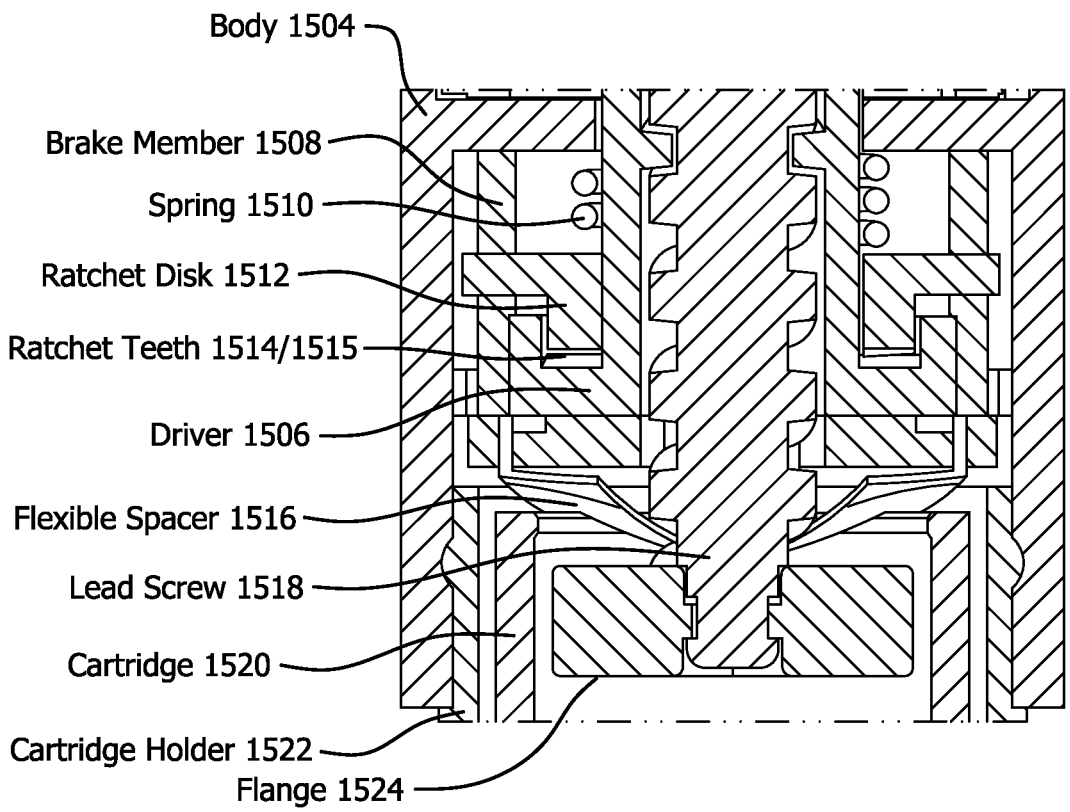
FIG. 15A is a partial cross-section view of a drive system for an injection pen according to an embodiment of the present disclosure.
Figure 15B:
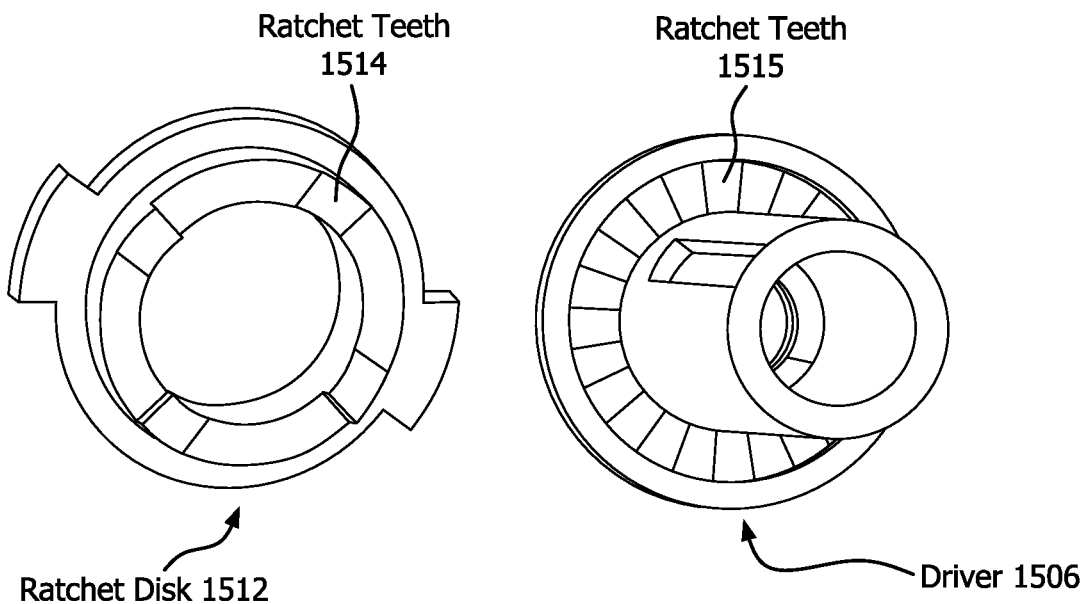
FIG. 15B is an perspective view of certain components of the drive system of FIG. 13A.
Figure 15C:
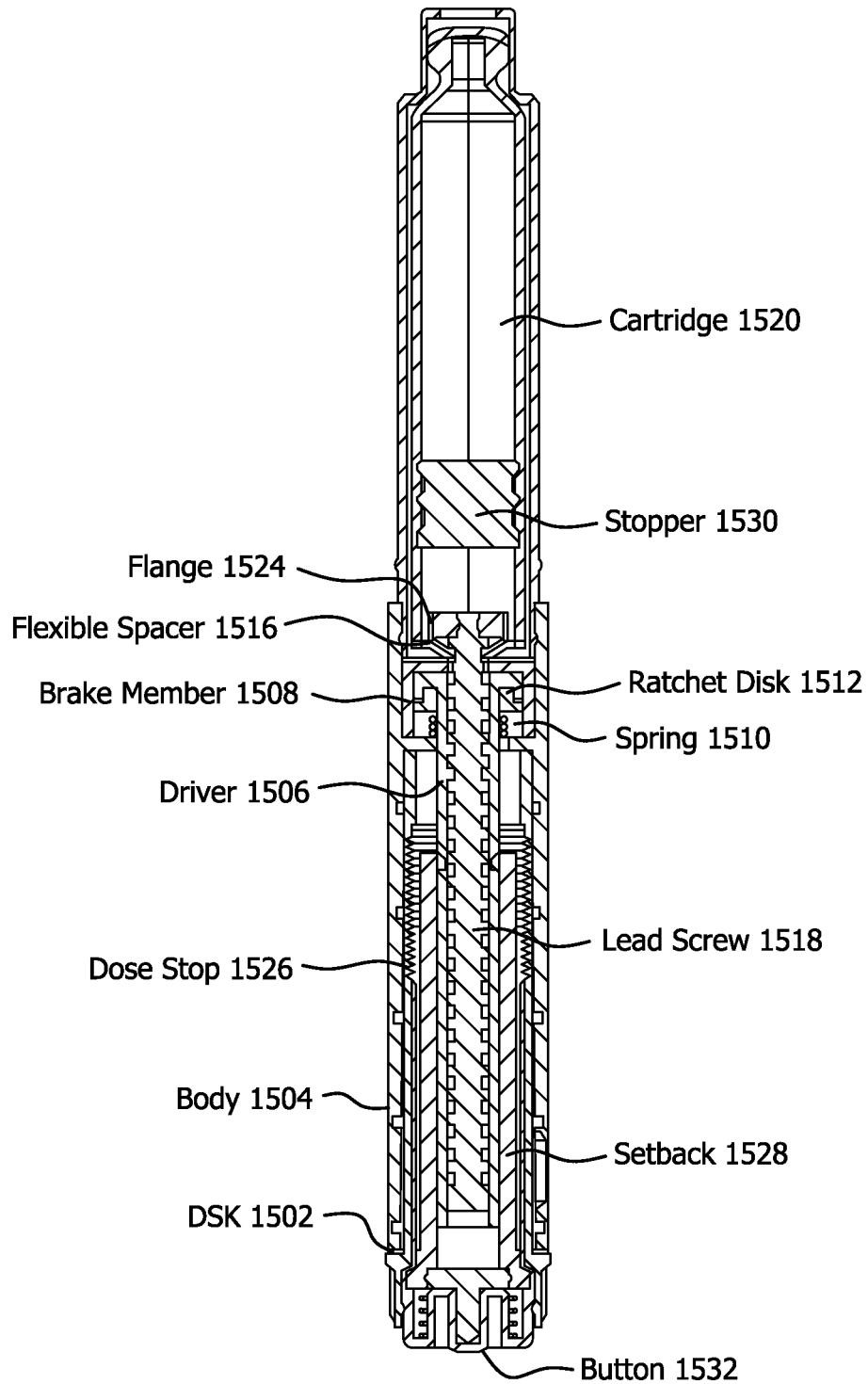
FIG. 15C is a cross-section view of a diagrammatical representation of an injection pen implementing the drive system of FIG. 13A.

Referring to FIGS. 15A, 15B, and 15C, an exemplary embodiment of a braking system includes a Ratchet Disk 1512 rotatably locked to a Brake Member 1508. An example of a pen-type injection device implementing such a braking system includes, for example as described above but without limitation and in any combination, other components such as: a button 1532, DSK 1502, setback 1528, and dose stop 1526 disposed in body 1504; flexible spacer 1516, lead screw 1518, cartridge 1520 containing medicament, cartridge holder 1522 (which contains cartridge 1520 and, for example can be removably attached to the body 1504 interacting with spacer 1516); and flange 1524 disposed at a distal end of the lead screw 1518 to engage a stopper 1530 disposed in the cartridge 1520. The Spring 1510 biases the Ratchet Disk 1512 toward the distal end of the Driver 1506. The Ratchet Disk 1512 has sloped surfaces facing the driven direction, and non-sloped surfaces facing the "dial" direction and constitute ratchet teeth 1514. The teeth 1514 interact with opposing teeth 1515 on the Driver 1506, which are spaced to correspond with the rotation of one dose of medicament. During dose injection the Driver 1506 rotates, forcing the Ratchet Disk 1512 to move axially as the ratchet teeth 1514/1515 slide past each other. After rotating to one dose increment the Ratchet Disk 1512 "clicks" into the base of the next sloped tooth 1515.

Figure 16A:
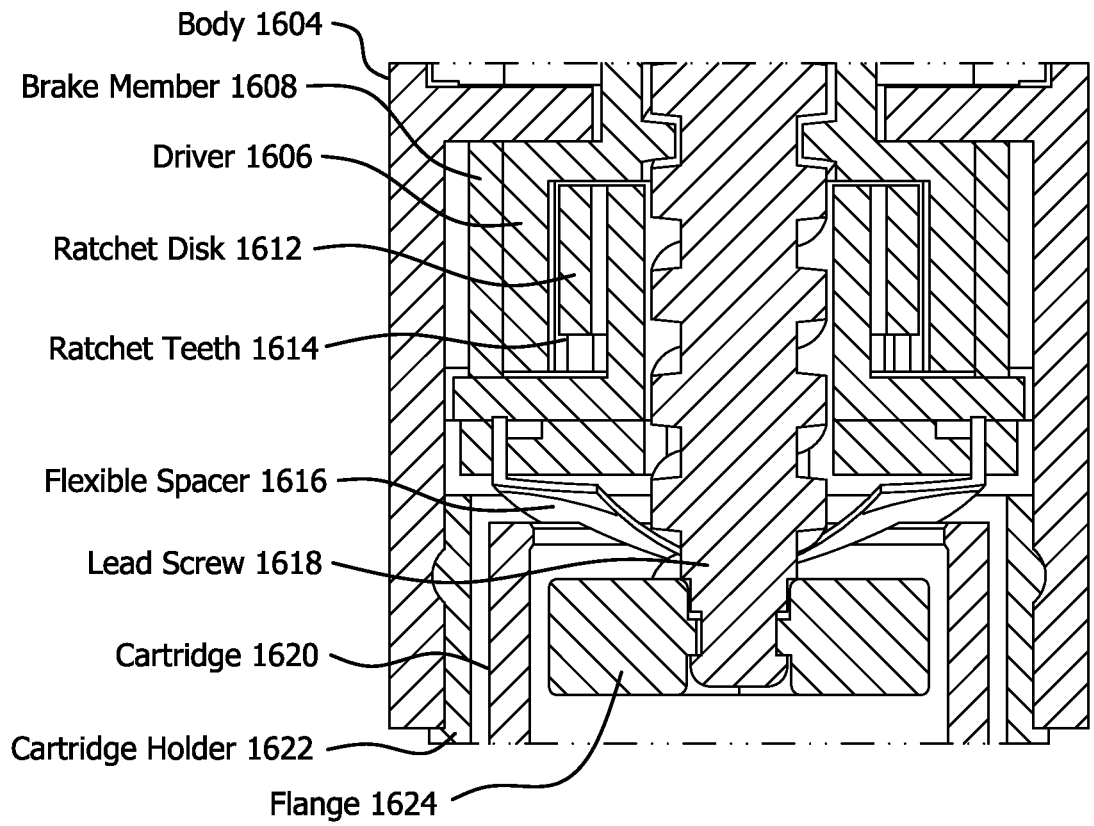
FIG. 16A is a partial cross-section view of a drive system for an injection pen according to an embodiment of the present disclosure.
Figure 16B:
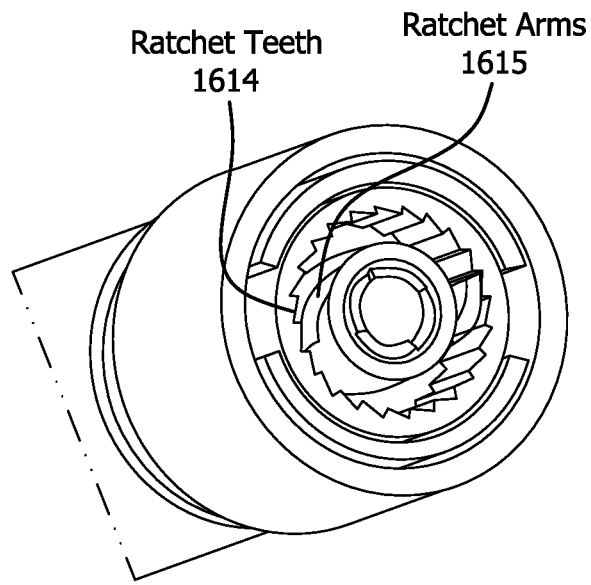
FIG. 16B is an perspective view of certain components of the drive system of FIG. 13A.
Figure 16C:
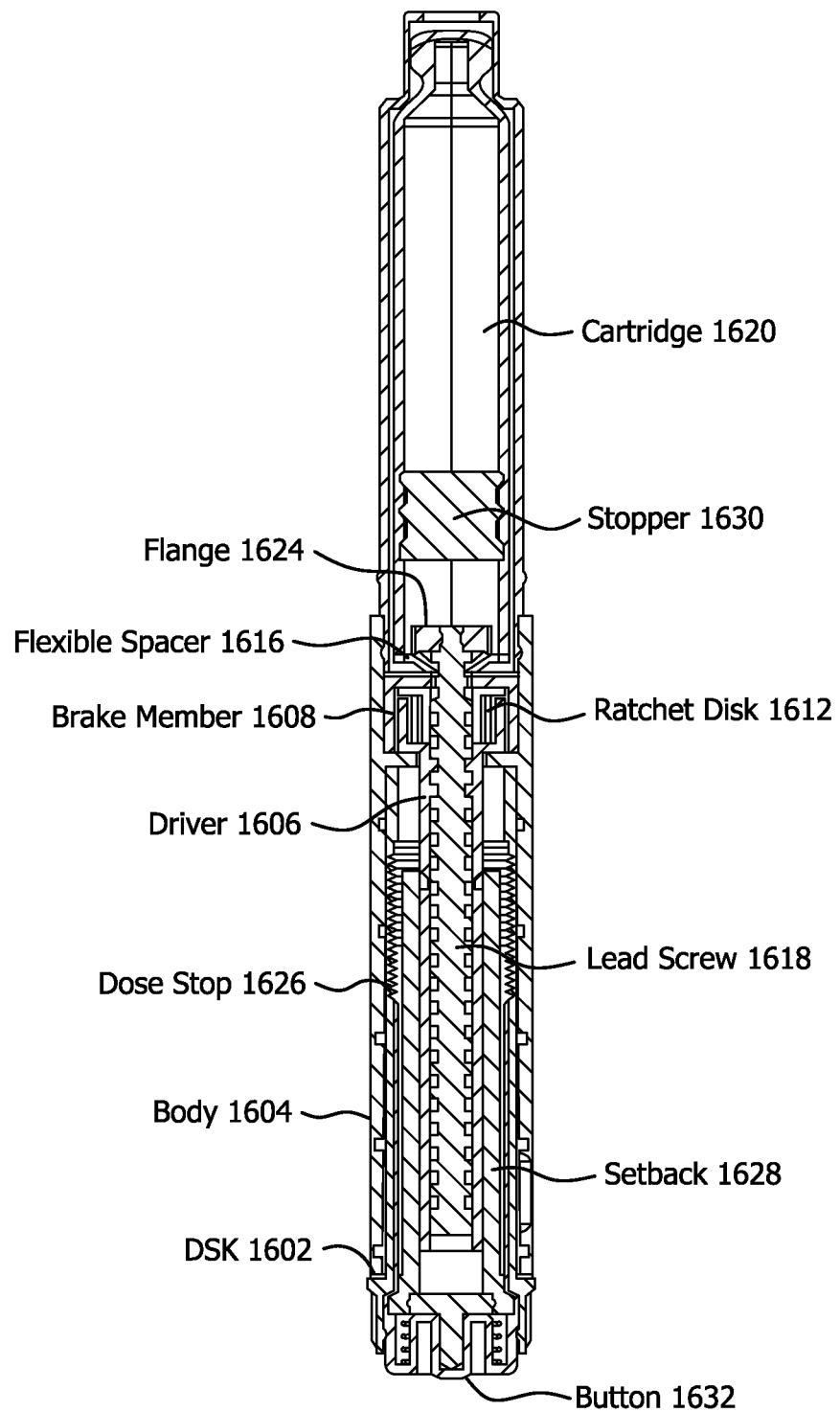
FIG. 16C is a cross-section view of a diagrammatical representation of an injection pen implementing the drive system of FIG. 13A.

Referring to FIGS. 16A, 16B, and 16C, an exemplary embodiment of a braking system includes a Ratchet Disk 1612 rotatably locked to a Brake Member 1608. An example of a pen-type injection device implementing such a braking system includes, for example as described above but without limitation and in any combination, other components such as: a button 1632, DSK 1602, setback 1628, and dose stop 1626 disposed in body 1604; flexible spacer 1616, lead screw 1618, cartridge 1620 containing medicament, cartridge holder 1622 (which contains cartridge 1620 and, for example can be removably attached to the body 1604 interacting with spacer 1616); and flange 1624 disposed at a distal end of the lead screw 1618 to engage a stopper 1630 disposed in the cartridge 1620. The Ratchet Disk 1612 has flexible ratchet arms 1615 that radiate outward toward the inward facing ratchet teeth 1614 of the Driver 1606. The Ratchet teeth 1614 of the driver 1606 are spaced to correspond with the rotation of one dose of medicament. During dose injection the Driver 1606 rotates, forcing the Ratchet arms 1615 to flex inward as the ratchet teeth 1614 slide past them. After rotating to one dose increment the Ratchet Disk 1612 "clicks" into the base of the next sloped tooth 1614.

Figure 17A:
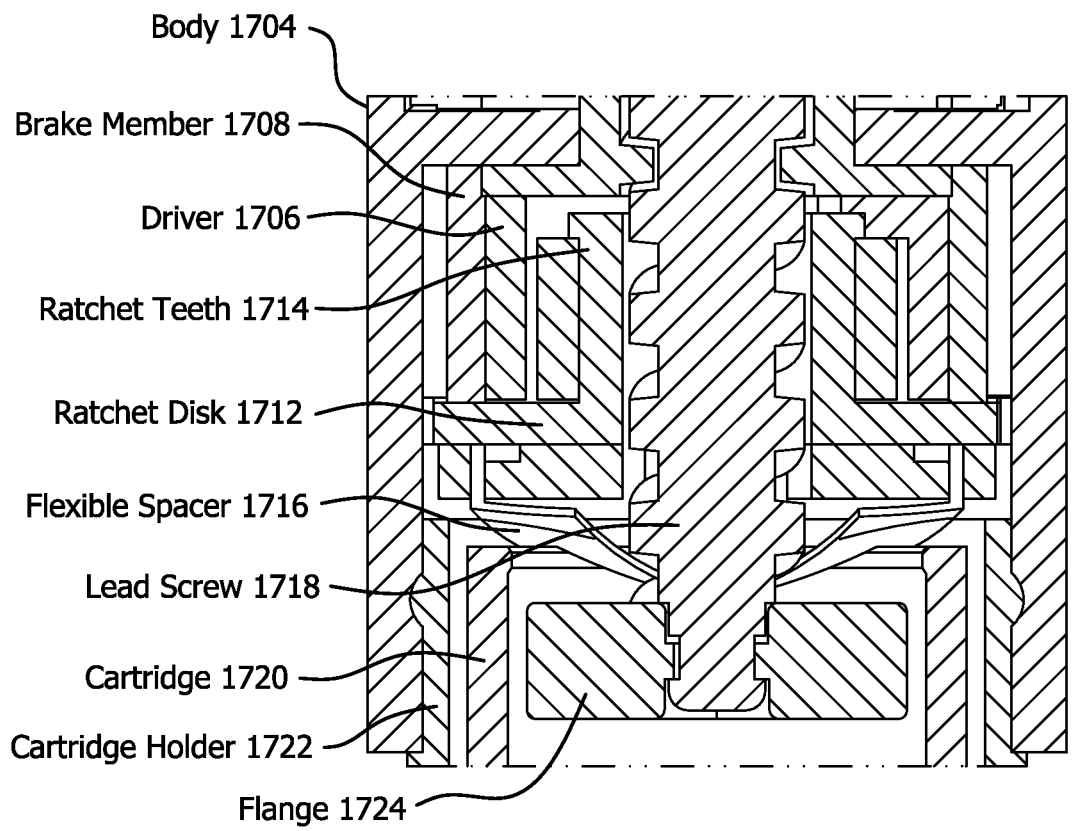
FIG. 17A is a partial cross-section view of a drive system for an injection pen according to an embodiment of the present disclosure.
Figure 17B:
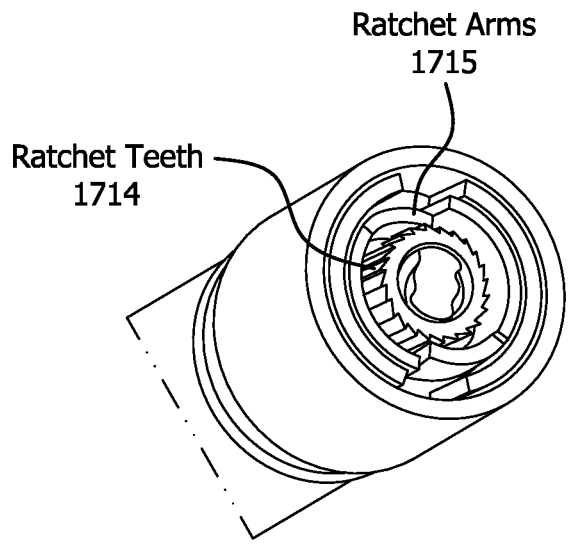
FIG. 17B is an perspective view of certain components of the drive system of FIG. 13A.
Figure 17C:
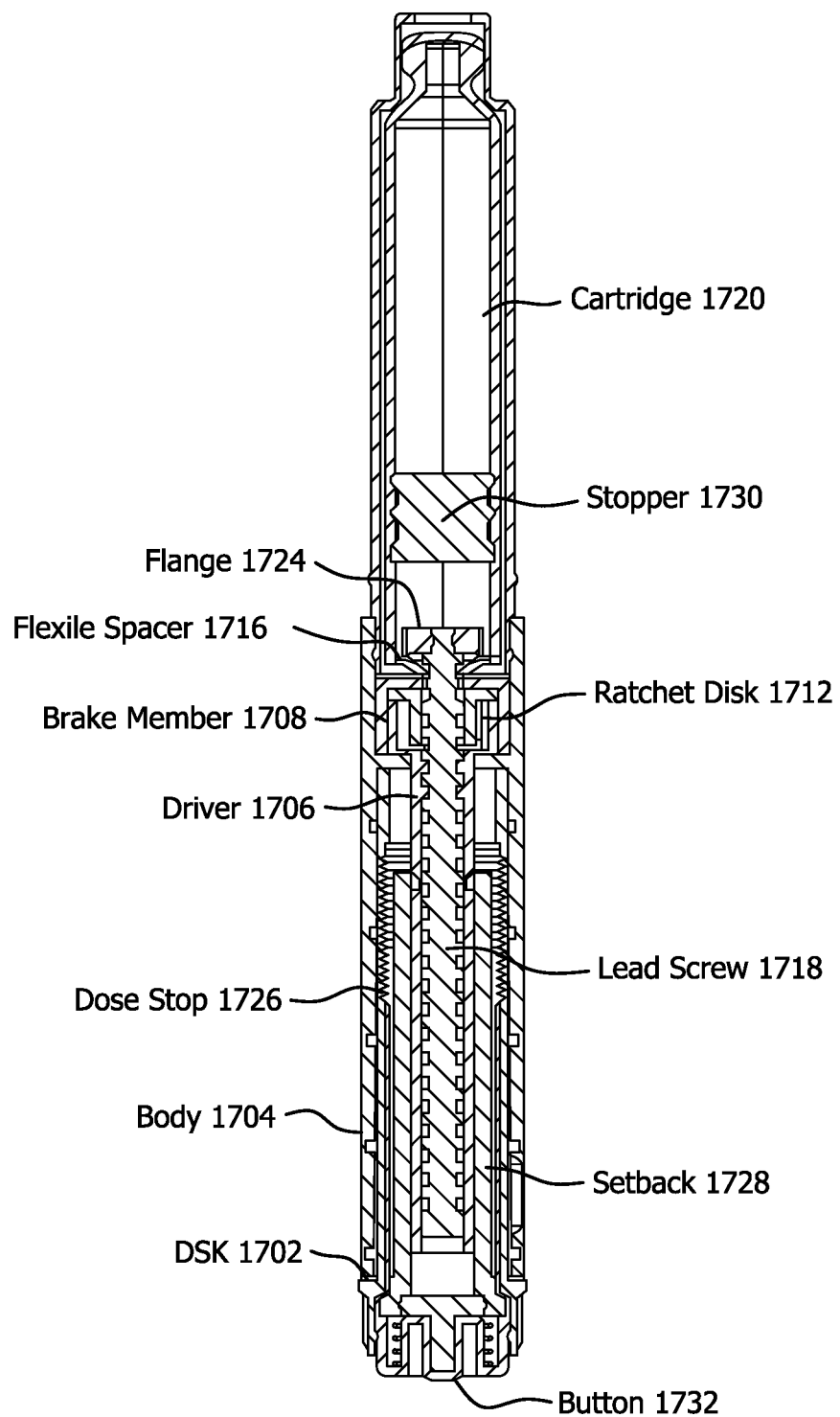
FIG. 17C is a cross-section view of a diagrammatical representation of an injection pen implementing the drive system of FIG. 13A.

Referring to FIGS. 17A, 17B, and 17C, an exemplary embodiment of a braking system includes a Ratchet Disk 1712 rotatably locked to a Brake Member 1708. An example of a pen-type injection device implementing such a braking system includes, for example as described above but without limitation and in any combination, other components such as: a button 1732, DSK 1702, setback 1728, and dose stop 1726 disposed in body 1704; flexible spacer 1716, lead screw 1718, cartridge 1720 containing medicament, cartridge holder 1722 (which contains cartridge 1720 and, for example can be removably attached to the body 1704 interacting with spacer 1716); and flange 1724 disposed at a distal end of the lead screw 1718 to engage a stopper 1730 disposed in the cartridge 1720. The Driver 1706 has flexible ratchet arms 1715 that radiate inward toward the outward facing ratchet teeth 1714 of the Ratchet Disk 1712. The Ratchet teeth 1714 of the Ratchet Disk 1712 are spaced to correspond with the rotation of one dose of medicament. During dose injection the Driver 1706 rotates, forcing its flexible ratchet arms 1715 to flex outward as they slide over the Ratchet teeth 1714. After rotating to one dose increment the Ratchet arms 1715 "click" into the base of the next sloped tooth 1714.

Figure 18A:
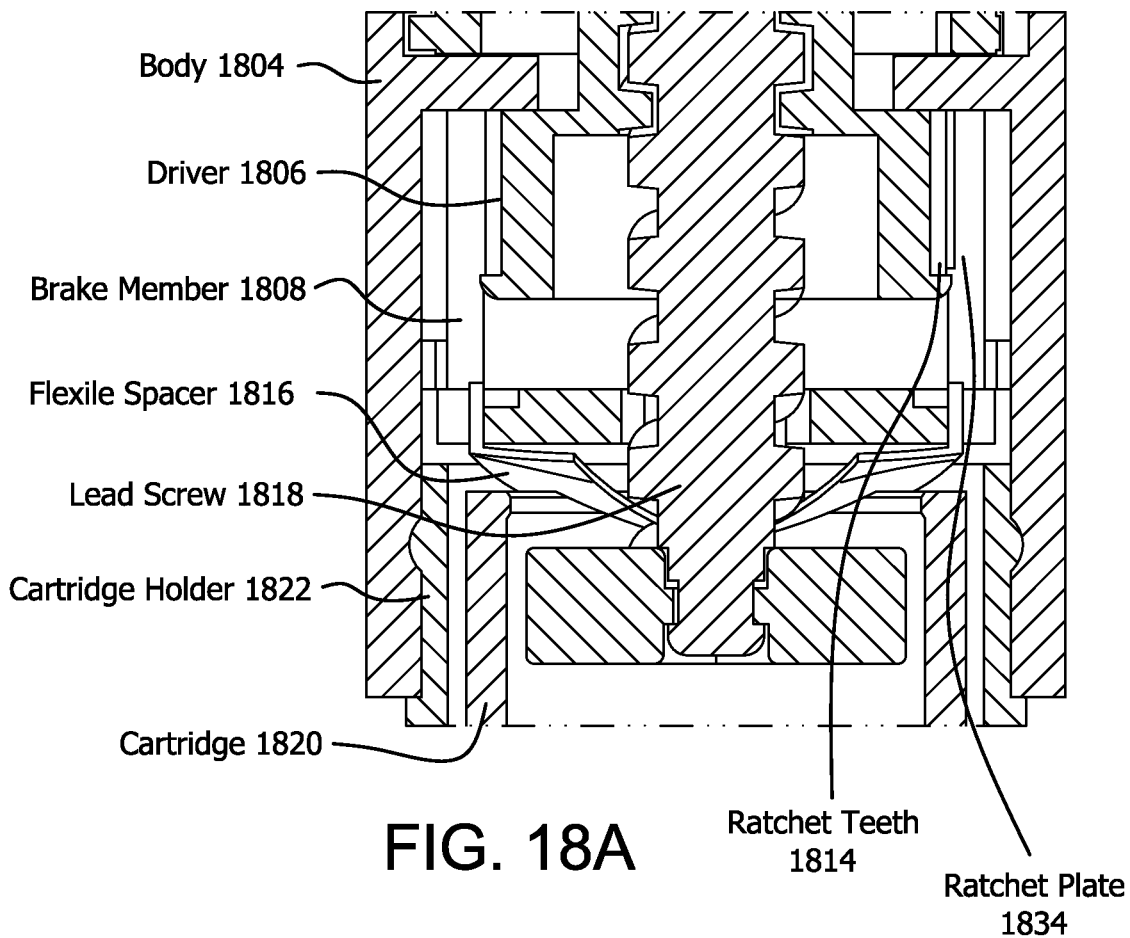
FIG. 18A is a partial cross-section view of a drive system for an injection pen according to an embodiment of the present disclosure.
Figure 18B:
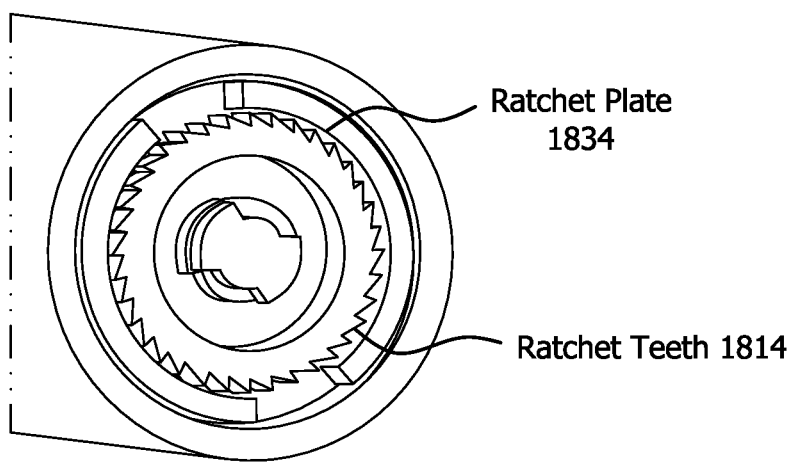
FIG. 18B is an perspective view of certain components of the drive system of FIG. 13A.
Figure 18C:
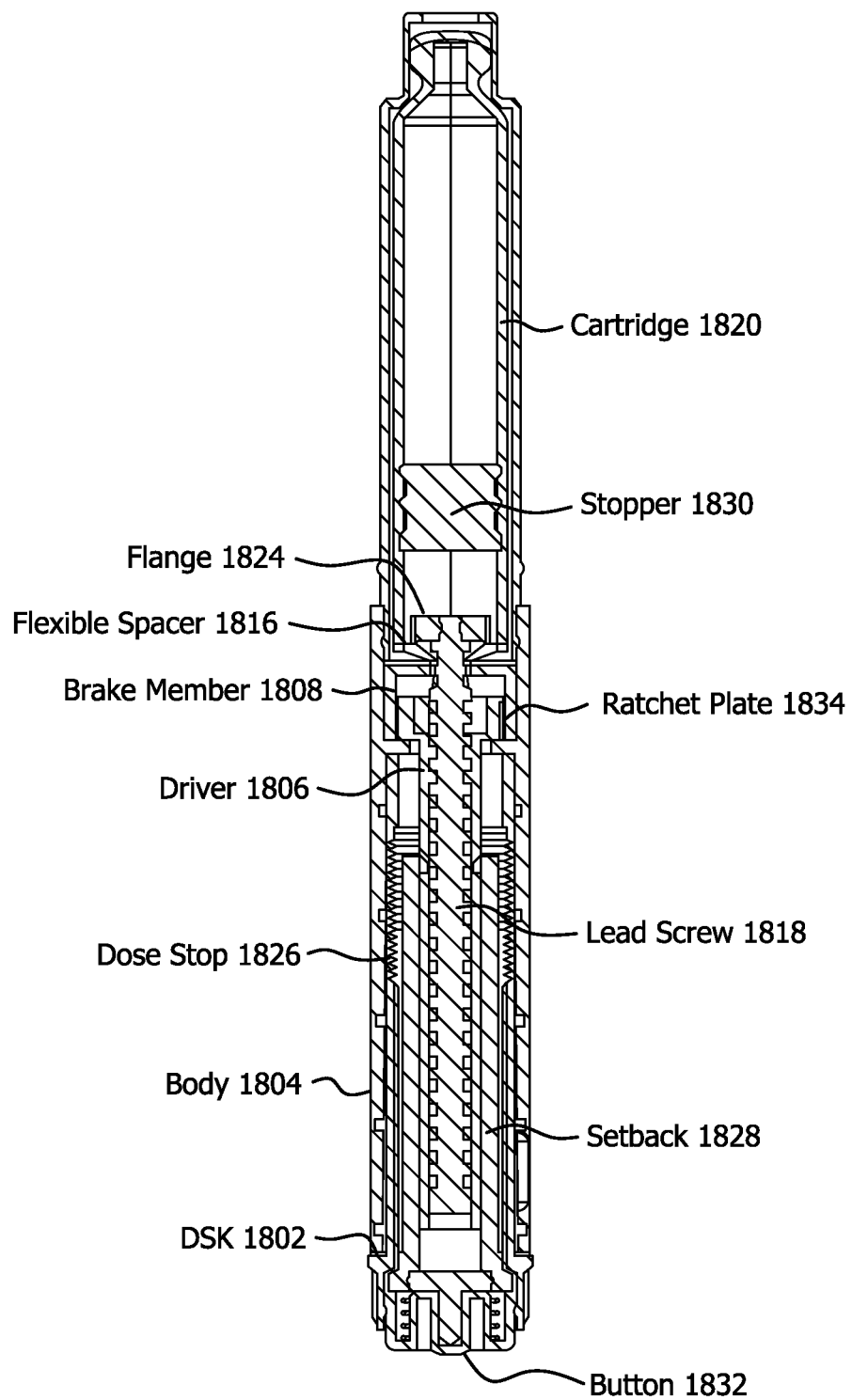
FIG. 18C is a cross-section view of a diagrammatical representation of an injection pen implementing the drive system of FIG. 13A.

Referring to FIGS. 18A, 18B, and 18C, an exemplary embodiment of a braking system includes a Ratchet Plate 1834 rotatably locked to a Brake Member 1808. An example of a pen-type injection device implementing such a braking system includes, for example as described above but without limitation and in any combination, other components such as: a button 1832, DSK 1802, setback 1828, and dose stop 1826 disposed in body 1804; flexible spacer 1816, lead screw 1818, cartridge 1820 containing medicament, cartridge holder 1822 (which contains cartridge 1820 and, for example can be removably attached to the body 1804 interacting with spacer 1816); and flange 1824 disposed at a distal end of the lead screw 1818 to engage a stopper 1830 disposed in the cartridge 1820. The Ratchet Plate 1834 has parabolic waves facing outward toward the Brake Member 1808. The Driver 1806 has sloped surfaces facing the driven direction, and non-sloped surfaces facing the "dial" direction and constitute ratchet teeth 1814. Ratchet teeth 1814 of the Driver are spaced to correspond with the rotation of one dose of medicament. During dose injection the Driver 1806 rotates, forcing the waves of the Ratchet plate 1834 to flex to allow the Ratchet teeth 1814 to rotate past the cavity walls. After rotating to one dose increment the Ratchet teeth 1814 "click" into the wall of the next Ratchet plate cavity.

Figure 19A:
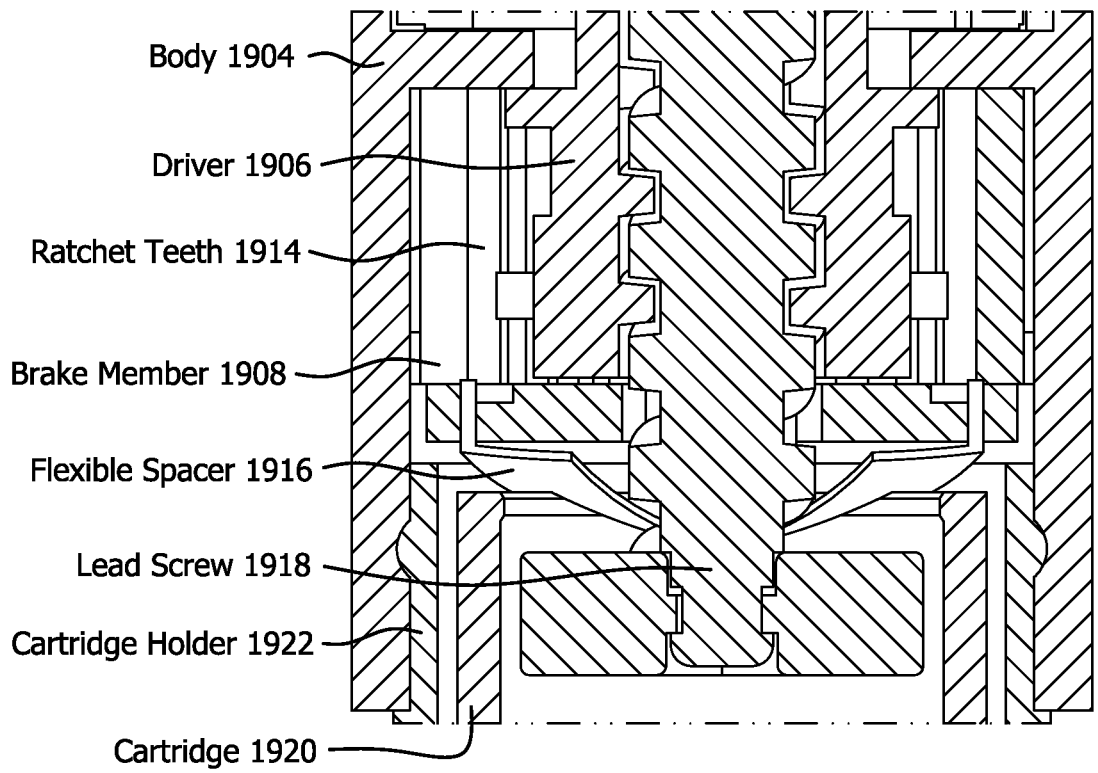
FIG. 19A is a partial cross-section view of a drive system for an injection pen according to an embodiment of the present disclosure.
Figure 19B:
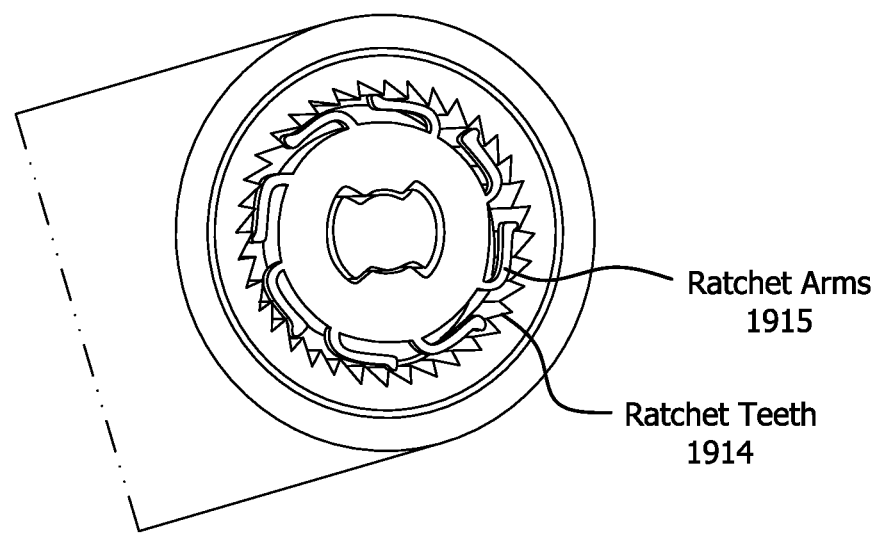
FIG. 19B is an perspective view of certain components of the drive system of FIG. 13A.
Figure 19C:
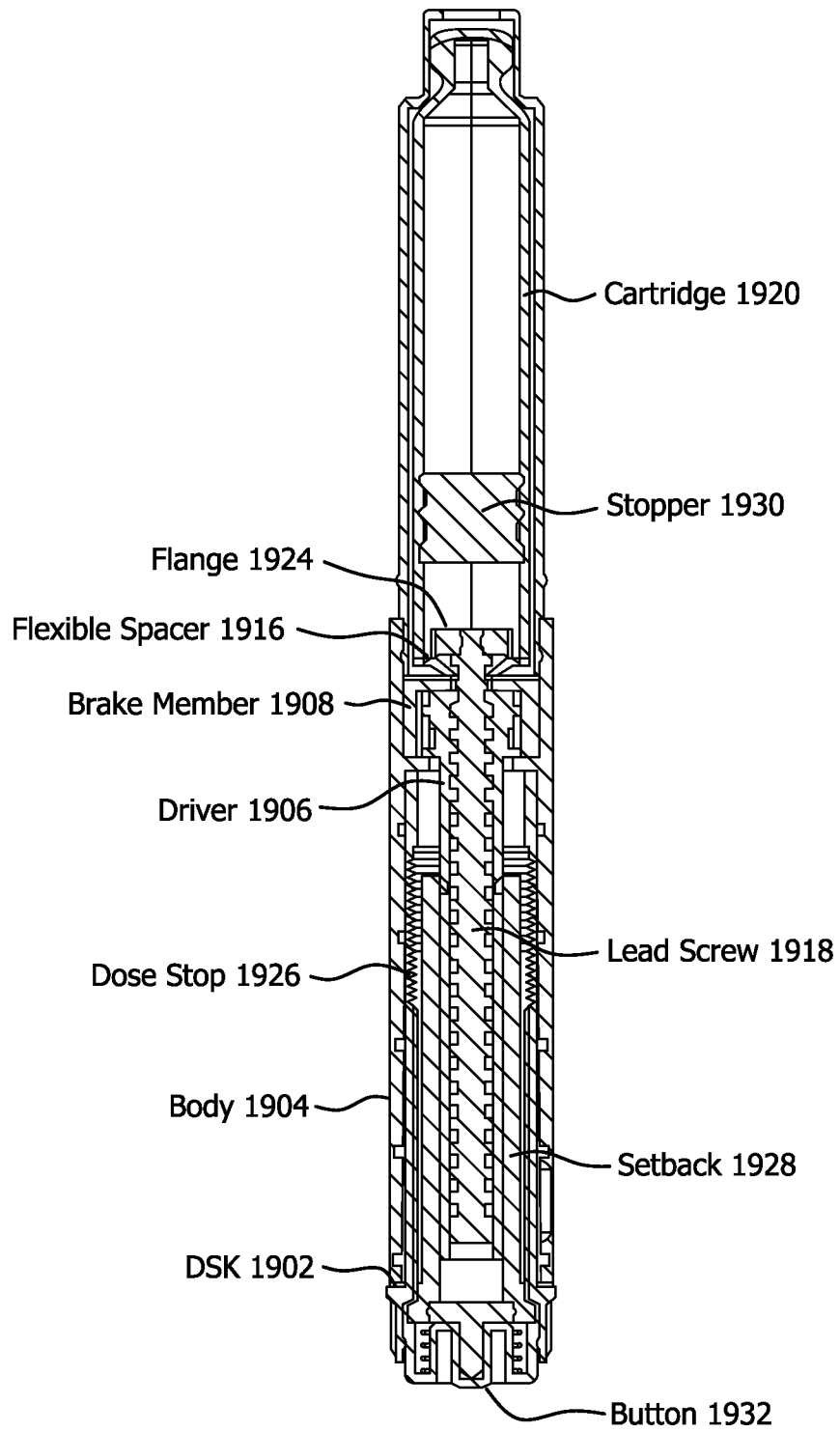
FIG. 19C is a cross-section view of a diagrammatical representation of an injection pen implementing the drive system of FIG. 13A.

Referring to FIGS. 19A, 19B, and 19C, an exemplary embodiment of a braking system includes a Driver 1906 having flexible ratchet 1915 arms that radiate outward toward the inward facing ratchet teeth 1914 of a Brake Member 1908. An example of a pen-type injection device implementing such a braking system includes, for example as described above but without limitation and in any combination, other components such as: a button 1932, DSK 1902, setback 1928, and dose stop 1926 disposed in body 1904; flexible spacer 1916, lead screw 1918, cartridge 1920 containing medicament, cartridge holder 1922 (which contains cartridge 1920 and, for example can be removably attached to the body 1904 interacting with spacer 1916); and flange 1924 disposed at a distal end of the lead screw 1918 to engage a stopper 1930 disposed in the cartridge 1920. The Ratchet teeth 1914 of the Brake Member 1908 are spaced to correspond with the rotation of one dose of medicament. During dose injection the Driver 1906 rotates, forcing its flexible ratchet arms 1915 to flex inward as they slide over the Ratchet teeth 1914. After rotating to one dose increment the Ratchet arms 1915 "click" into the base of the next sloped tooth 1914.

Figure 20A:
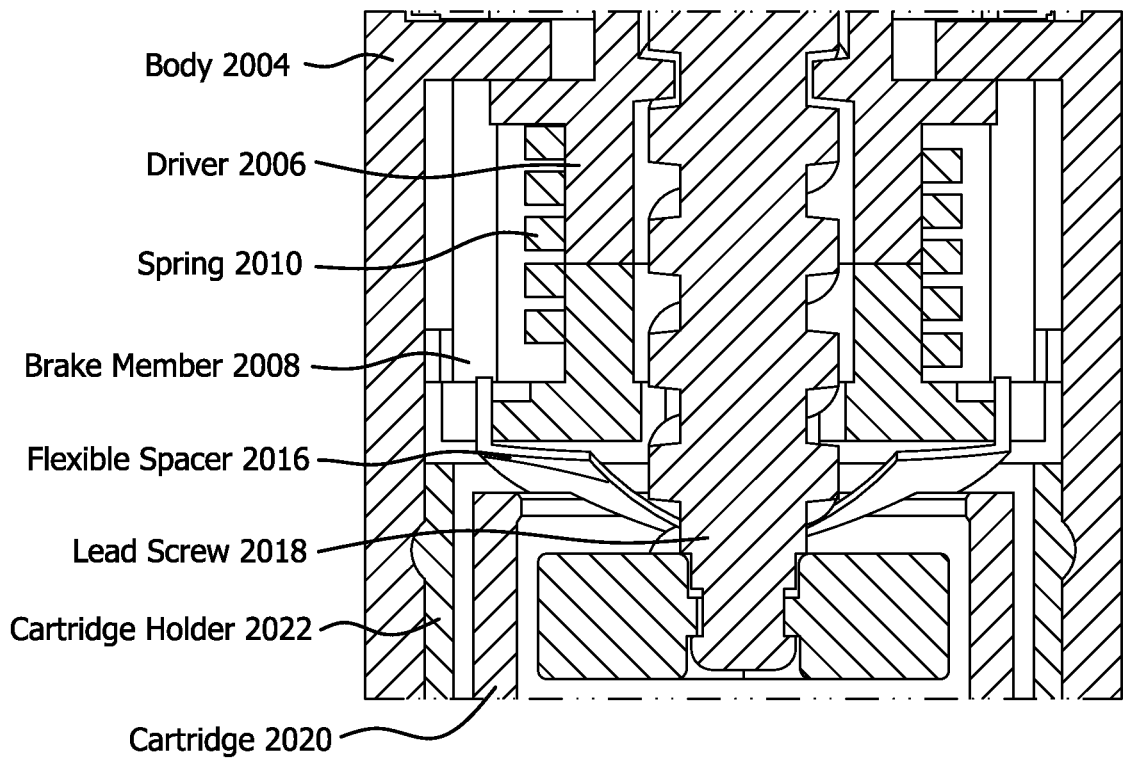
FIG. 20A is a partial cross-section view of a drive system for an injection pen according to an embodiment of the present disclosure.
Figure 20B:
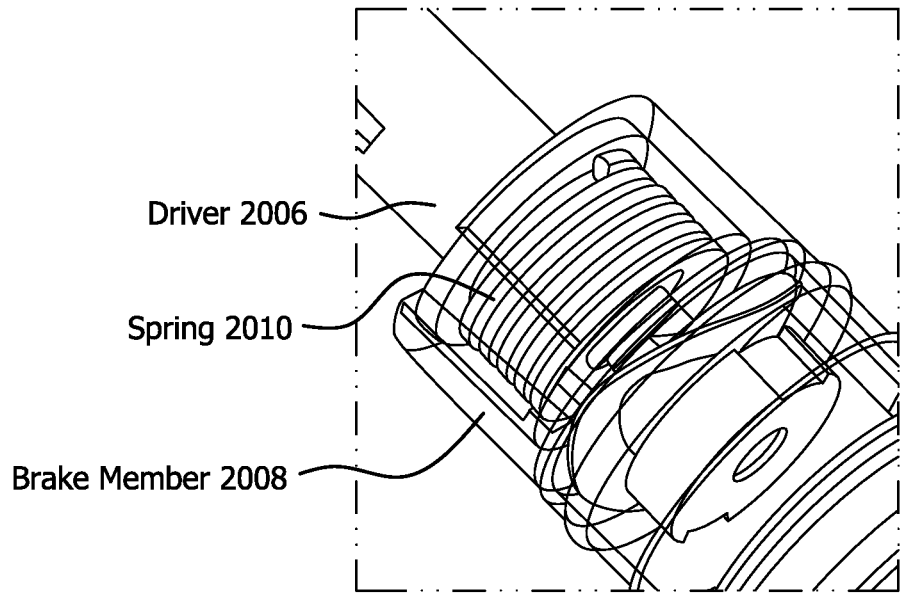
FIG. 20B is an perspective view of certain components of the drive system of FIG. 13A.
Figure 20C:
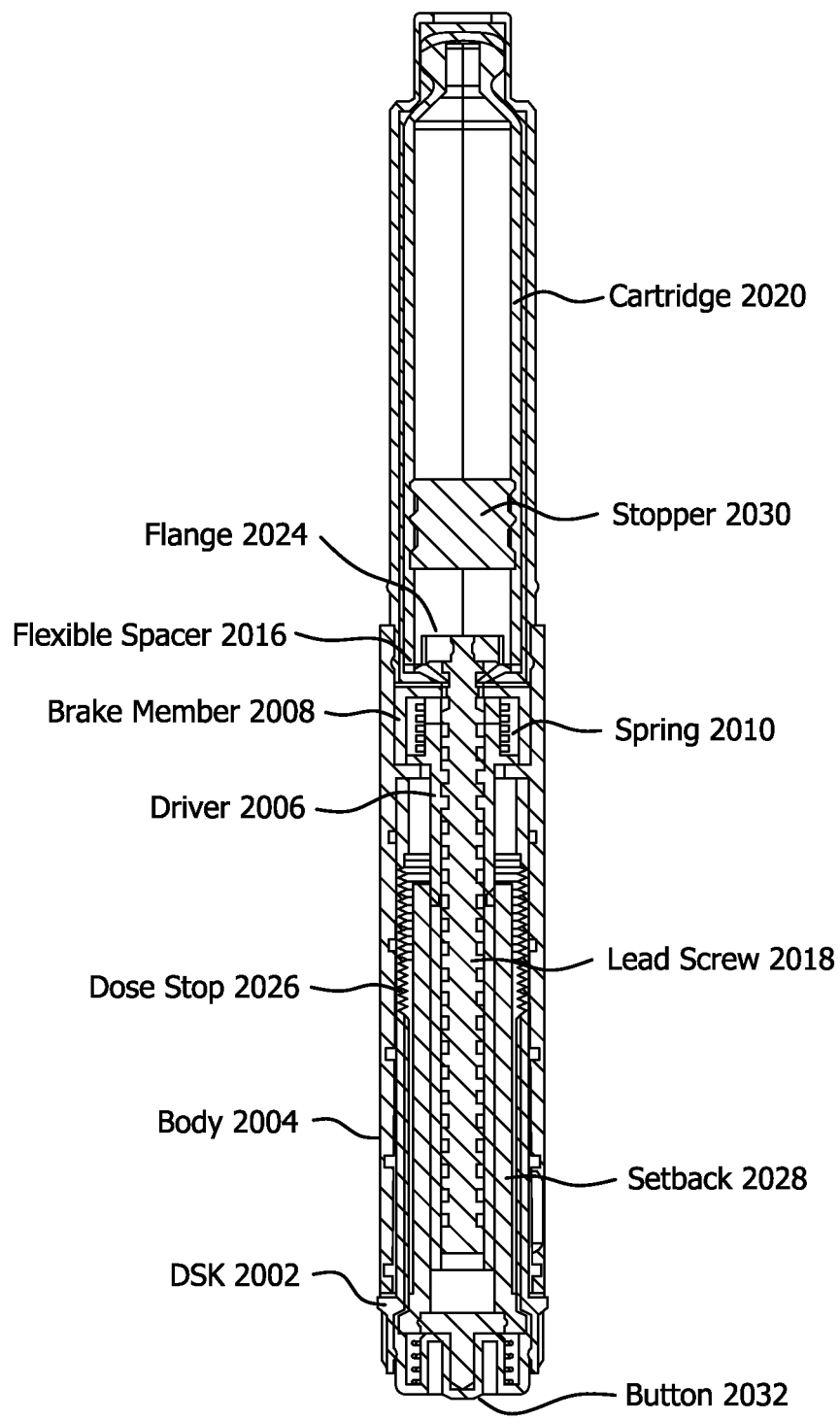
FIG. 20C is a cross-section view of a diagrammatical representation of an injection pen implementing the drive system of FIG. 13A.

Referring to FIGS. 20A, 20B, and 20C, an exemplary embodiment of a braking system includes a coil Spring 2010 positioned around the head of the Driver 2006. An example of a pen-type injection device implementing such a braking system includes, for example as described above but without limitation and in any combination, other components such as: a button 2032, DSK 2002, setback 2028, and dose stop 2026 disposed in body 2004; flexible spacer 2016, lead screw 2018, cartridge 2020 containing medicament, cartridge holder 2022 (which contains cartridge 2020 and, for example can be removably attached to the body 1304 interacting with spacer 1316); and flange 2024 disposed at a distal end of the lead screw 2018 to engage a stopper 2030 disposed in the cartridge 2020. The Spring 2010 is rotatably locked to the Brake Member 2008 which is rotatably locked to the Body 2004. The coil Spring 2010 is oriented to grip the driver 2006 and prevent Driver 2006 from rotating during dialing. If the Driver 2006 starts to rotate backwards the Spring 2010 tightens around it, preventing it from rotating back. When the driver 2006 starts to rotate in the Injection direction, the spring 2010 loosens (unwinds) slightly, relieving its grip on the Driver 2006 and allowing it to rotate. Clicking during dose injection can be created by a weak clicker (not shown) that is not configured to prevent rotation.

Figure 21A:
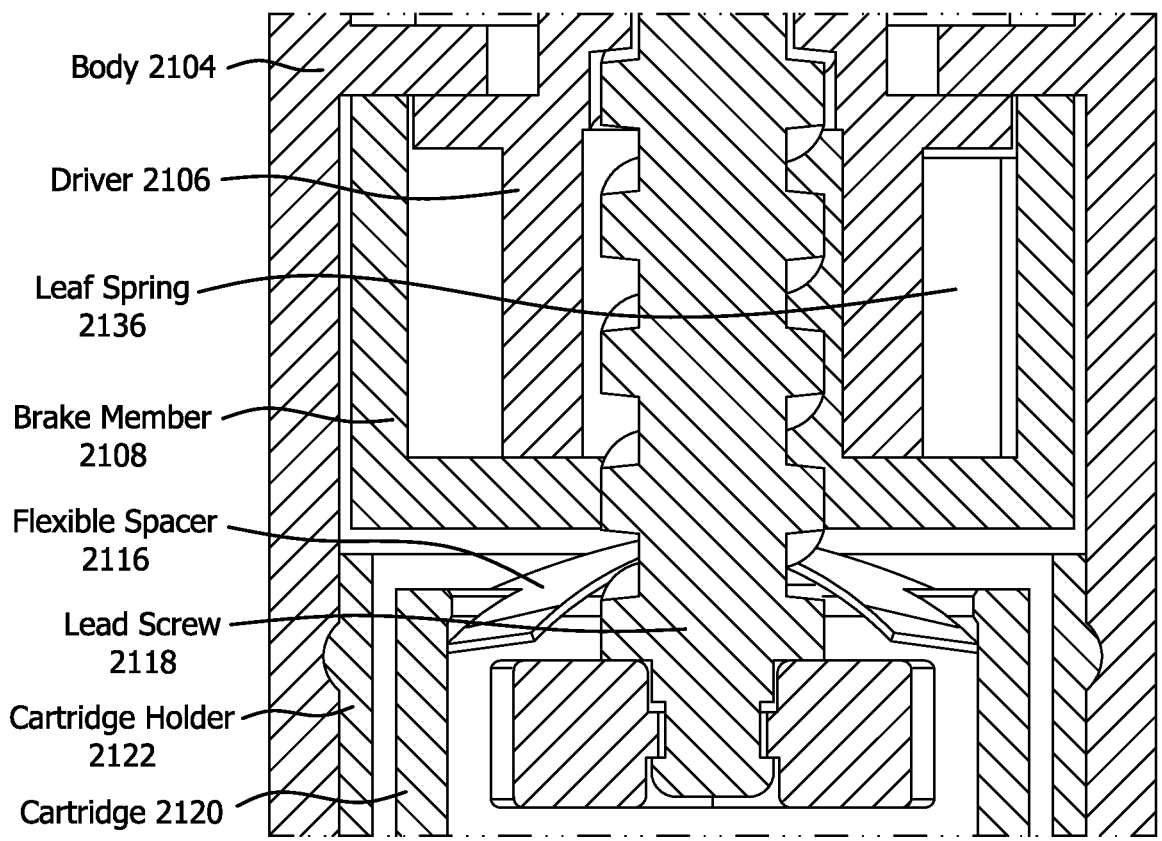
FIG. 21A is a partial cross-section view of a drive system for an injection pen according to an embodiment of the present disclosure.
Figure 21B:
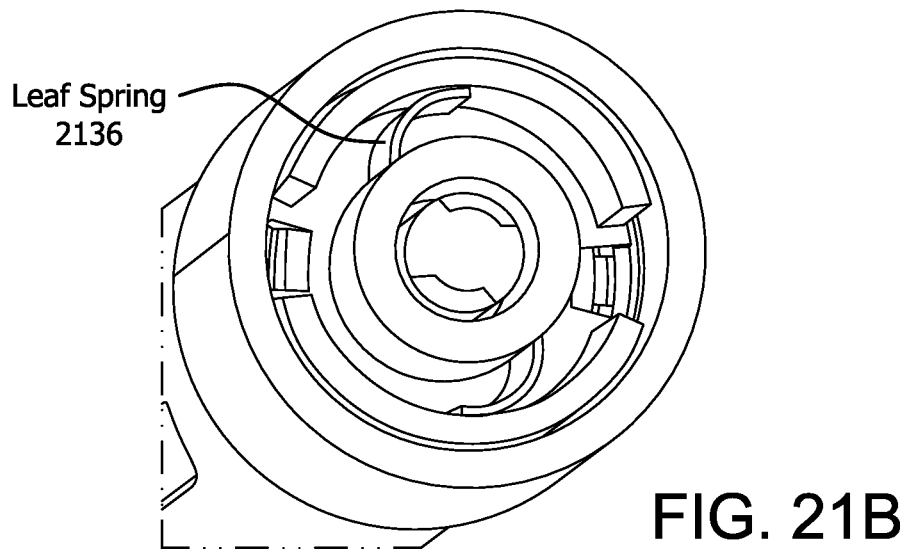
FIG. 21B is an perspective view of certain components of the drive system of FIG. 22A is a partial cross-section view of a drive system for an injection pen according to an embodiment of the present disclosure.
Figure 21C:
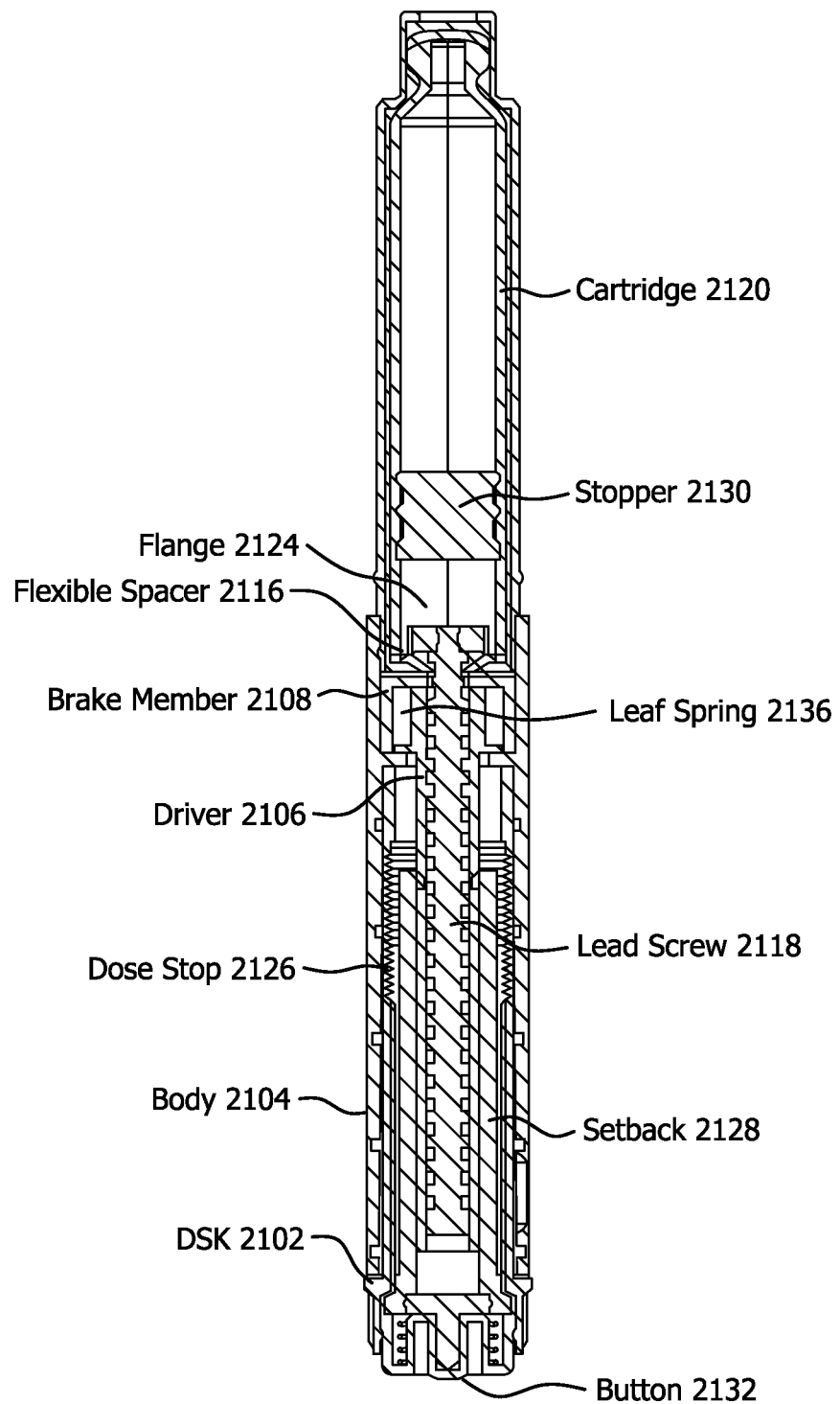
FIG. 21C is a cross-section view of a diagrammatical representation of an injection pen implementing the drive system of FIG. 13A.

Referring to FIGS. 21A, 21B, and 21C, an exemplary embodiment of a braking system includes one or more Leaf Spring(s) 2136 positioned around the head of the Driver 2106. An example of a pen-type injection device implementing such a braking system includes, for example as described above but without limitation and in any combination, other components such as: a button 2132, DSK 1302, setback 2128, and dose stop 2126 disposed in body 2104; flexible spacer 2116, lead screw 2118, cartridge 2120 containing medicament, cartridge holder 2122 (which contains cartridge 2120 and, for example can be removably attached to the body 2104 interacting with spacer 2116); and flange 2124 disposed at a distal end of the lead screw 2118 to engage a stopper 2130 disposed in the cartridge 2120. The Spring(s) 2136 are rotatably locked to the Brake Member 2108 which is rotatably locked to the Body 2104. The Spring(s) 2136 are oriented to grip the Driver 2106 and prevent it from rotating during dialing. If the Driver 2106 starts to rotate backwards the Springs 2136 tighten around it, preventing it from rotating back. When the driver 2106 starts to rotate in the Injection direction, the Spring(s) 2136 loosen slightly, relieving their grip on the Driver 2106 and allowing it to rotate. Clicking during dose injection can be created by a weak clicker (not shown) that is not configured to prevent rotation.

Figure 22A:
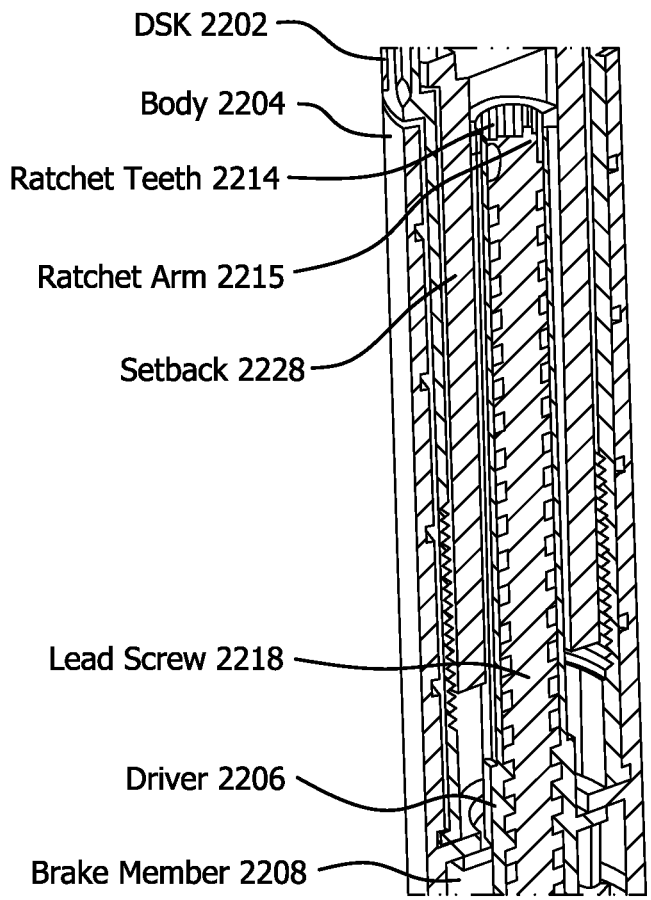
FIG. 22B is an perspective view of certain components of the drive system of FIG. 13A.
FIG. 22C is a cross-section view of a diagrammatical representation of an injection pen implementing the drive system of FIG. 13A.
Figure 22B:
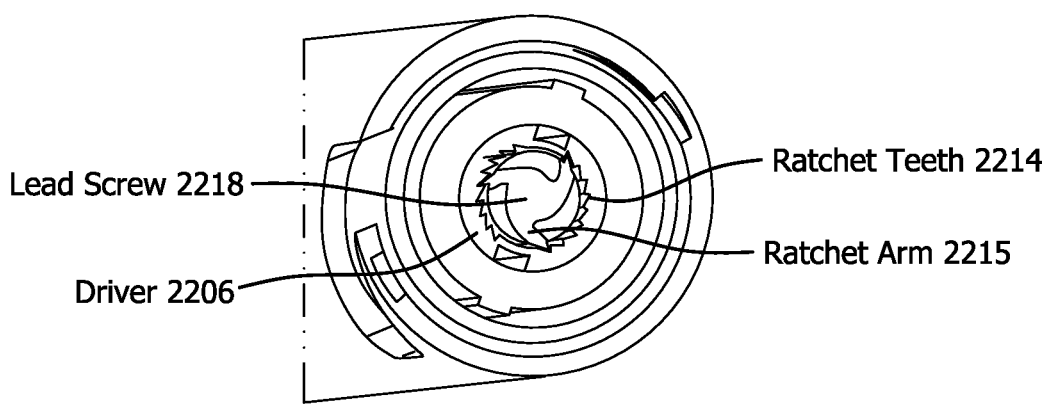
Figure 22C:
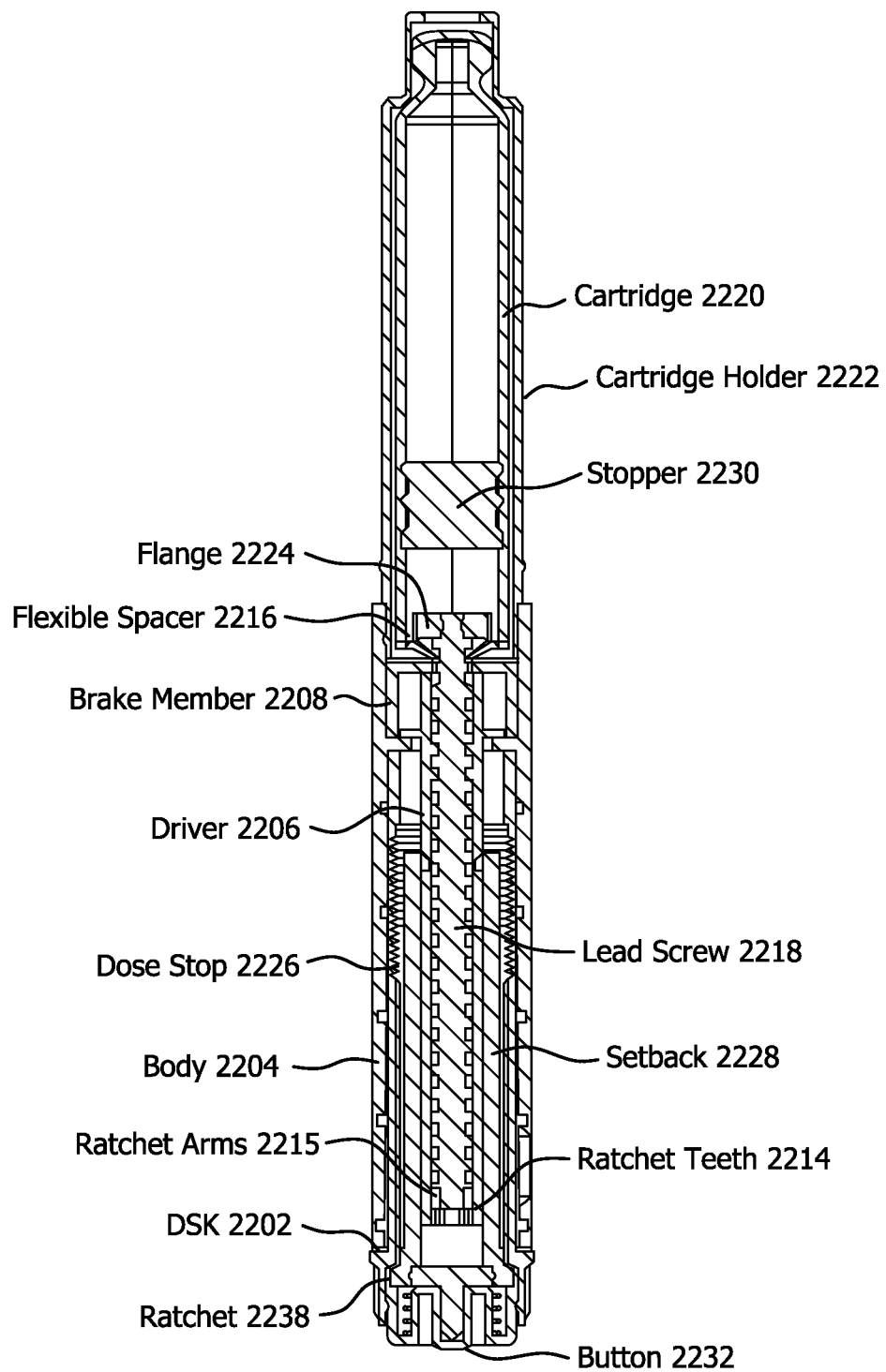

Referring to FIGS. 22A, 22B, and 22C, an exemplary embodiment of a braking system includes a Lead screw 2218 with flexible Ratchet arms 2215 that can be disposed at a proximal end thereof, and that radiate outward toward the inward facing Ratchet teeth 2214 of the Driver 2206. An example of a pen-type injection device implementing such a braking system includes, for example as described above but without limitation and in any combination, other components such as: a button 2232, DSK 2202, setback 2228, and dose stop 2226 disposed in body 2204; flexible spacer 2216, lead screw 2218, cartridge 2220 containing medicament, cartridge holder 2222 (which contains cartridge 2220 and, for example can be removably attached to the body 2204 interacting with spacer 2216); and flange 2224 disposed at a distal end of the lead screw 2218 to engage a stopper 2230 disposed in the cartridge 2220. The Ratchet teeth 2214 of the Driver 2206 are spaced to correspond with the rotation of one dose of medicament. The Lead Screw 2218 is rotatably fixed to the Body 2204 via the Brake Member 2208. During dose injection the Driver 2206 rotates, forcing the flexible Ratchet arms 2215 of the Lead screw 2218 to flex inward as they slide over the Ratchet teeth 2214. After rotating to one dose increment the Ratchet arms 2215 "click" into the base of the next sloped tooth 2214.

According to an exemplary embodiment, because the lead screw 23 is non-rotatable with respect to the body 1, as the driver 21 is caused to rotate during injection, as described above due to its rotational coupling with the setback member 9, the lead screw 23 through its threaded engagement with the driver 21 is caused to move in the distal direction to press against the stopper 34 disposed in the medicament cartridge 18, thus expelling a liquid medication therefrom. The lead screw 23 is prevented from moving in the proximal direction because the driver 21 is rotatable in only a single direction (that which results in distal movement of the lead screw 23) due to the one-way ratchet between the driver 21 and the ratchet disk 43 of the brake member 36. Thus, accurate dosing can be ensured because the lead screw 23 maintains its engagement with the stopper 34 between injections. A mechanical advantage is preferably provided such that the dose set knob 2 moves further in the axial direction than the lead screw 23 during the injection, reducing the injection force that must be applied by the user. This is preferably accomplished by providing different pitches for the threaded connection between the dose set knob 2 and the pen upper body 1 and the threaded connection between the driver 21 and the lead screw 23. The ratio between the thread pitches can vary depending on the liquid medication and the expected dose volumes. For example, the pitch ratio can be 4.35:1 or 3.25:1, but is not limited thereto.

Figure 7C:
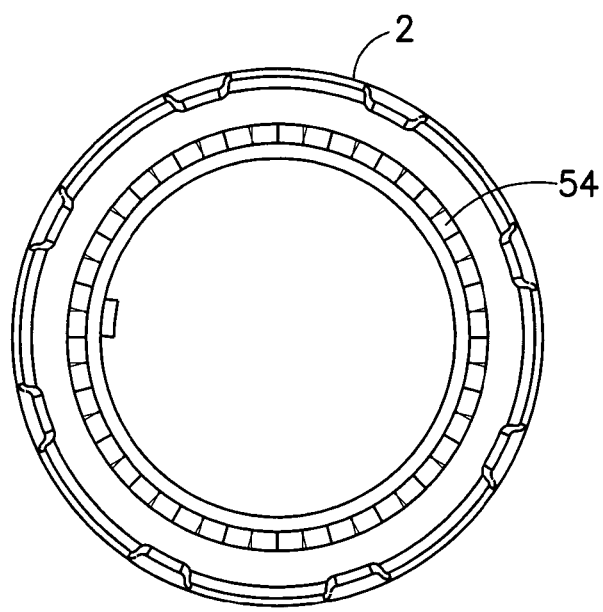
FIG. 7C is a proximal end elevational view of the dose set knob of FIG. 7A.

According to an exemplary non-limiting implementation, a dose stop member 71 (FIGS. 2 and 4) that can be provided for last dose management, to prevent the setting of a dose that is larger than the remaining amount of medication in the cartridge 18. The dose stop member 71 is axially slidable but rotationally fixed with respect to the setback member 9 by being positioned between a pair of splines 63 provided on an outer surface 64 of the setback member 9, as shown in FIGS. 2, 5A and 5B. The dose stop member 71 can be a half-nut like element that is threaded on its outer surface with a plurality of threads. The dose stop member threads 72 are configured to engage with corresponding threads 65 provided on an inner surface 66 of the dose set knob 2, as shown in FIGS. 7A-7C. Initially, the dose stop member 71 is threadedly engaged with one or two of the proximal-most threads of threads 65 provided on the dose set knob 2. During dose setting, as the dose set knob 2 rotates relative to the setback member 9 and therefore also the dose stop member 71, the dose stop member 71 is caused to slide in the distal direction by a distance corresponding to the set dose due to its engagement with the threads 65 in the dose set knob 2.

Figure 7D:
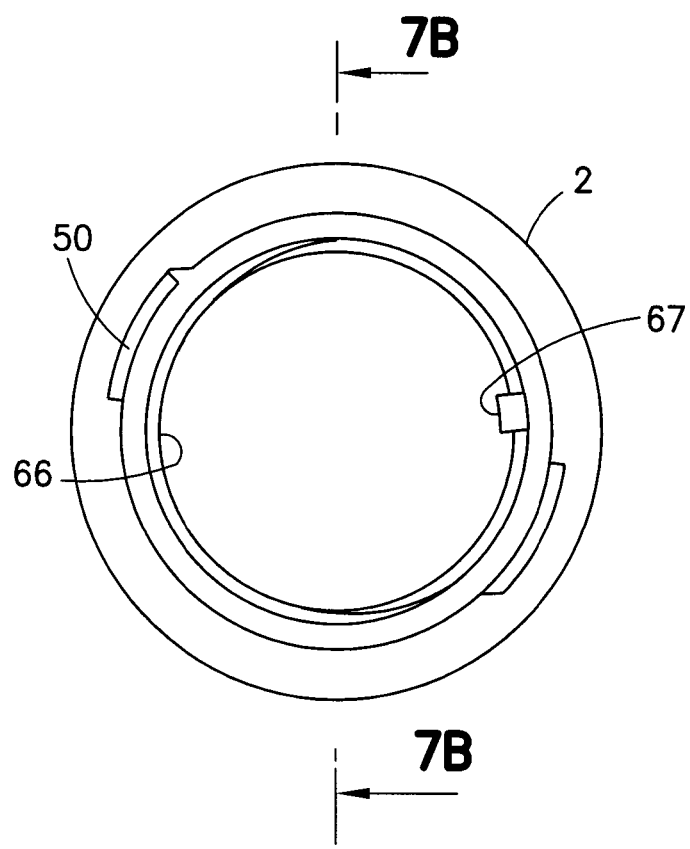
FIG. 7D is a distal end elevational view of the dose set knob of FIG. 7A.

During injection, because the setback member 9 and the dose set knob 2 are rotationally coupled as discussed above, the dose stop member 71 maintains its position relative to the threads 65 of the dose set knob 2. The dose stop member 71 moves in the distal direction during dose setting until a distal edge 73 (FIG. 4) of the dose stop member 71 abuts an inwardly directed key 67 provided on the inner surface 66 of the dose set knob 2, as shown in FIGS. 7B and 7D. In this position, the dose stop member 71 is prevented from further movement in the distal direction which also prevents further rotation of the dose set knob 2 to set an additional dose. In its final position, the dose stop member 71 is threadedly engaged with approximately two of the distal most threads of the threads 65 provided in the dose set knob 2. As shown in FIG. 7B, the total distance traveled by the dose stop member 71 from its initial position to its final position when it abuts key 67 provided on the dose set knob 2, is greater than the length of either of the thread portions provided on the dose stop member 71 and the dose set knob 2, respectively.

FIGS. 23-27 illustrate an exemplary implementation of an audible and/or tactile signaling and/or feedback mechanism with respect to an exemplary embodiments of injection pen including the components illustrated in FIGS. 1-12, and any of the driver mechanisms illustrated and described below with reference to FIGS. 13A through 22C. The exemplary embodiment depicted in FIGS. 23-27 includes a clicker body 751 that can be disposed with respect to a proximal end 709 of setback member, such as a setback member 9, and a proximal end 702 of a dose set knob, such as dose set knob 2. The remaining components and functions of the injection pen are substantially similar to the injection pen 11 implementing any of the driver mechanisms illustrated and described below with reference to FIGS. 1 through 2C.

Figure 23:
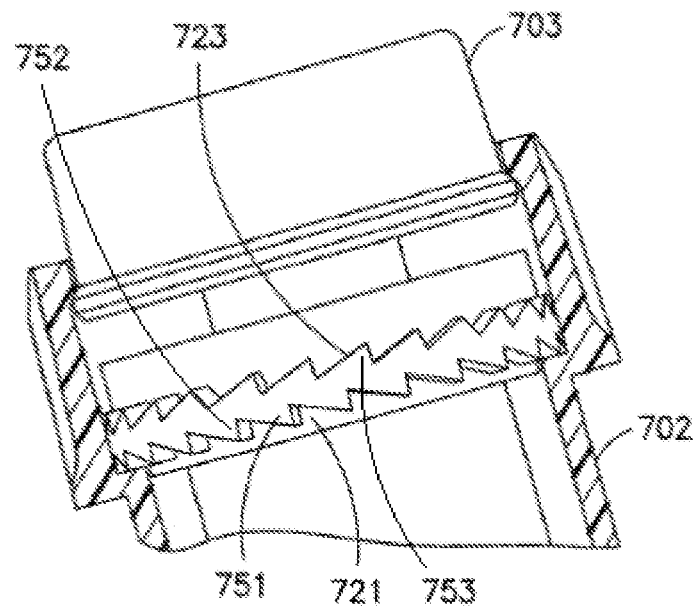
FIG. 23 is an elevational view in cross-section of a clicker body disposed between a dose set knob and a setback member of an injection pen in accordance with an exemplary embodiment of the present disclosure.
Figure 24:
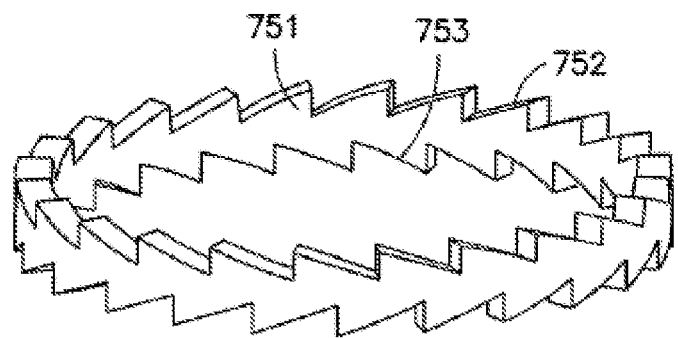
FIG. 24 is a perspective view of the clicker body of FIG. 23.
Figure 25:
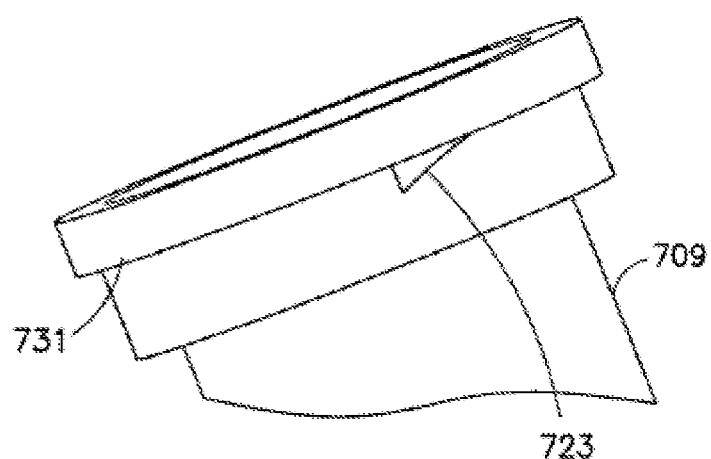
FIG. 25 is partial perspective view of the setback member of the injection pen of FIG. 23.
Figure 26:
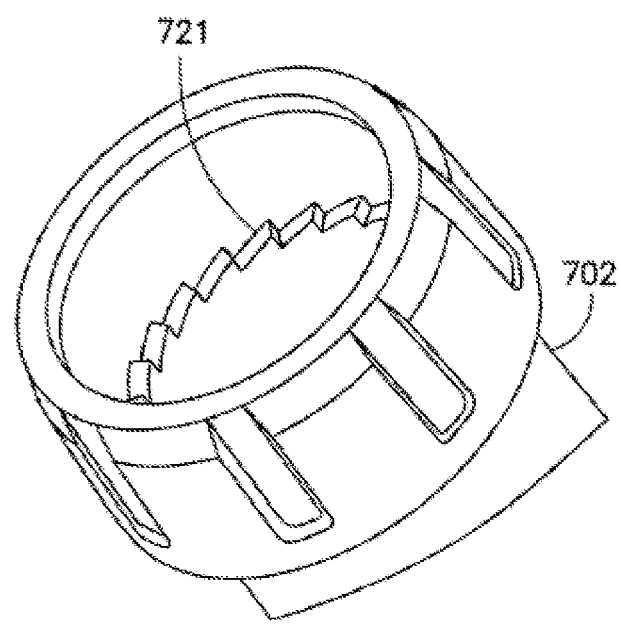
FIG. 26 is a partial perspective view of the dose set knob of the injection pen of FIG. 13.
Figure 27:
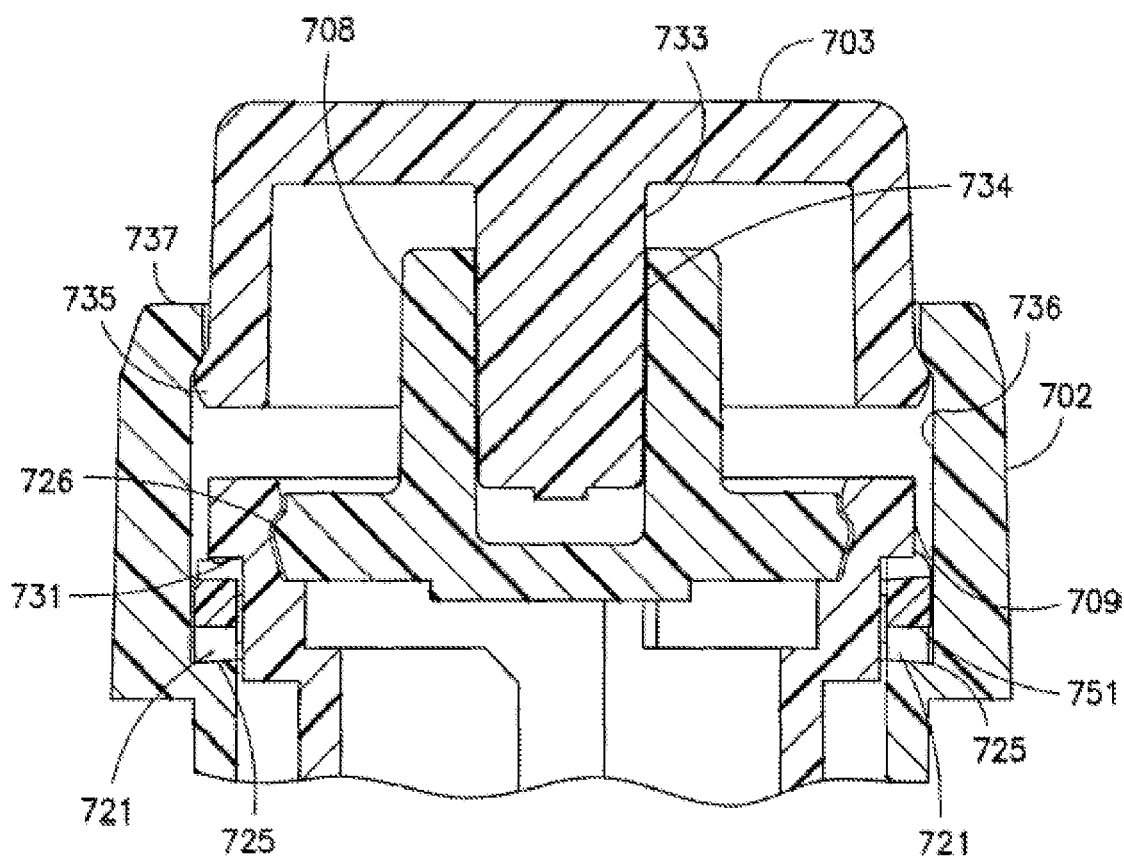
FIG. 27 is an elevational view in cross-section of the injection pen of FIG. 73.

Referring to FIGS. 23-27, the clicker body 751 can be substantially ring-shaped having an upper set of teeth 752 and a lower set of teeth 753, as shown in FIGS. 23 and 24. In an exemplary implementation, the upper teeth 752 and the lower teeth 753 can each have a sloped surface and a stopping surface. For example, the upper teeth 752 can have a sloped surface that is opposite that of the lower teeth 753. Preferably, the sloped surfaces of the upper teeth 752 and the lower teeth 753 form an angle of approximately 15 degrees. As shown in FIGS. 23 and 27, the clicker body 751 can be disposed between a proximal end 702 of a dose set knob and a proximal end 709 of a setback member. For example, clicker body 751 can be disposed between an annular shoulder 725 of the proximal end 702 of a dose set knob and an enlarged portion 731 of the proximal end 709 of a setback member. A plurality of teeth 721 having a sloped surface and a stopping surface can be configured to extend axially in the proximal direction from the shoulder 725. A plurality of teeth 723 having a sloped surface and a stopping surface can be configured to extend axially in the distal direction from the enlarged portion 731.

The clicker body 751 facilitates generating a tactile signal or clicking noise during dose setting. For example, the upper teeth 752 of the clicker body 751 can be locked to the teeth 721 (FIG. 26) of the dose set knob via respective teeth locking surfaces such that the clicker body 751 rotates with the dose set knob as the dose set knob advances out of the pen upper body. The lower teeth 753 of the clicker body 751 slide over the teeth 723 (FIG. 25) of the setback member 709 via respective teeth sliding surfaces, thereby generating a tactile signal or clicking noise to indicate to the user that a dose is being set.

The clicker body 751 also facilitates generating a tactile signal or clicking noise during dose correcting. For example, the lower teeth 753 of the clicker body 751 can be locked to the teeth 723 (FIG. 25) of the setback member via respective teeth locking surfaces such that the clicker body 751 is rotatably locked to the setback member. Rotation of the dose set knob as the dose set knob is advanced back into pen upper body to correct the dose causes the teeth 721 (FIG. 26) of the dose set knob to slide over the upper teeth 752 of the clicker body 751 via respective teeth sliding surfaces, thereby generating a tactile signal or clicking noise to indicate to the user that a dose is being corrected. Accordingly, the clicker body 751 facilitates generating a tactile signal or clicking noise during both dose setting and dose correcting.

An exemplary configuration of a push button 703 is illustrated in FIGS. 23 and 27 having the following features. Optionally, a bearing insert 708 can be received in an annular groove 726 configured in proximal end 709, as shown in FIG. 17. Optionally, push button 703 can have a projection 733 received by an opening 734 in the bearing insert 708. Optionally, a distal skirt 735 of the push button 703 can be slidably received by a recess 736 adjacent portion 737 of the proximal end 702. Optionally, bearing insert 708 and a setback member are integrally formed. Optionally, a spring, such as spring 10, can be deployed with respect to push button 703 and proximal end 709 of setback member, for example to bias push button 703 with respect to setback member. Such a configuration can further facilitate relative slippage and locking of the respective teeth of the clicker, dose set knob, and setback member.

In an exemplary implementation, once a desired dose is set, the user pushes the push button 703 for injection such that under the force applied by the user pressing the push button 703, the setback member is moved into a locking or meshing engagement with the dose set knob via a meshing of the respective teeth 723 of the setback member, the lower teeth 753 and the upper teethe 752 of the clicker body 751, and teeth 721 of the dose set knob. In case of an optional implementation of a spring, such as spring 10, the force applied by the user pressing the push button 703 for injection is sufficient to overcome the biasing force of the spring, thereby compressing the spring to facilitate the meshing of the respective teeth 723 of the setback member, the lower teeth 753 and the upper teethe 752 of the clicker body 751, and teeth 721 of the dose set knob.

Optionally, when the dose set knob and the setback member rotate together during an injection, the clicker body 751 does not rotate relative to either the dose set knob or the setback member, the clicker body 751 does not generate a tactile signal or clicking noise when injecting a set dose.

Optionally, a reverse locking and slipping of the respective teeth can be achieved, for example, by flipping clicker body with respect to the proximal ends of the dose set knob and setback member, and reconfiguring slipping and stopping surfaces of the teeth of the dose set knob and the setback member accordingly. In such an implementation, the audible and/or tactile signaling and/or feedback during dose setting and dose correcting would simply be reversed.

While the present disclosure has been shown and described with reference to particular illustrative embodiments, it is not to be restricted by such exemplary embodiments. It is to be appreciated that those skilled in the art can change or modify the exemplary embodiments without departing from the scope and spirit of the present disclosure.

We claim:

1. A medication injection pen, comprising:
   a cartridge housing which houses a medication cartridge;
   a housing connected to said cartridge housing;
   a dose set knob rotatable with respect to said housing;
   a dose stop member to prevent setting of a dose that is larger than a remaining amount of medication in the cartridge;
   a driver;
   a ratchet disk rotatably locked to said driver; and
   a brake member rotatably locked to said housing,
   wherein
   during the setting of the dose and dose correcting,
      said ratchet disk is rotatably locked to said driver,
      said ratchet disk and said brake member are rotationally fixed with respect to each other, to prevent said driver from rotating with said dose set knob, and
      said dose stop member rotates relative to said dose set knob, and
   during an injection,
      said ratchet disk is rotatably locked to said driver,
      said driver moves into locking engagement with said dose set knob and said ratchet disk can move axially with respect to said driver and away from said brake member to allow said driver to rotate with said dose set knob, and
      said dose stop member does not rotate relative to said dose set knob.

2. The medication injection pen according to claim 1 wherein
   said ratchet disk comprises first teeth including first sloped surfaces and first non-sloped surfaces, and said brake member comprises second teeth includes second sloped surfaces and second non-sloped surfaces,
   during the setting of the dose and the dose correcting, said first teeth engage said second teeth to substantially prevent said driver from rotating with said dose set knob, and
   during the injection, said driver moves into locking engagement with said dose set knob thereby overcoming friction between said first sloped surfaces and said second sloped surfaces to allow said driver to rotate with said dose set knob.

3. The medication injection pen according to claim 2, wherein
   during said injection, after rotating to a dose increment, said ratchet disk moves into a position with respect to said brake member where at least one of said first teeth move into a base of a next of said second teeth.

4. The medication injection pen according to claim 2, wherein
   said second teeth are spaced to correspond with the rotation of one dose of the medication.

5. The medication injection pen according to claim 1, wherein
   a spring member biases said ratchet disk toward said brake member.

6. The medication injection pen according to claim 5, wherein during said injection, said ratchet disk rotates with said driver and moves against said spring member as first sloped surfaces ride over second slope surfaces of said brake member.

* * * * *